(12) United States Patent
Kawazoe et al.

(10) Patent No.: US 9,598,373 B2
(45) Date of Patent: Mar. 21, 2017

(54) METHOD FOR PRODUCING 4,4,7-TRIFLUORO-1,2,3,4-TETRAHYDRO-5H-1-BENZAZEPINE COMPOUND AND INTERMEDIATE USED IN THE METHOD

(71) Applicant: TACURION, Bridgewater, NJ (US)

(72) Inventors: Souichirou Kawazoe, Tokyo (JP); Takahiro Akiba, Tokyo (JP); Kiichi Sato, Tokyo (JP); Akio Miyafuji, Tokyo (JP); Kazuyoshi Obitsu, Tokyo (JP); Junji Itoh, Tokyo (JP); Shun Hirasawa, Tokyo (JP); Hiroyuki Koshio, Tokyo (JP)

(73) Assignee: TACURION, Bridgeport, NJ (US)

( * ) Notice: Subject to any disclaimer, the term of this patent is extended or adjusted under 35 U.S.C. 154(b) by 0 days.

(21) Appl. No.: 14/406,568

(22) PCT Filed: Jun. 11, 2013

(86) PCT No.: PCT/JP2013/066076
§ 371 (c)(1),
(2) Date: Dec. 9, 2014

(87) PCT Pub. No.: WO2013/187406
PCT Pub. Date: Dec. 19, 2013

(65) Prior Publication Data
US 2015/0141641 A1    May 21, 2015

(30) Foreign Application Priority Data
Jun. 11, 2012   (JP) .................................. 2012-131504

(51) Int. Cl.
| | | |
|---|---|---|
| C07D 223/16 | (2006.01) |
| C07C 311/21 | (2006.01) |
| C07C 51/09 | (2006.01) |
| C07C 51/367 | (2006.01) |
| C07C 67/31 | (2006.01) |
| C07C 303/40 | (2006.01) |
| C07D 301/00 | (2006.01) |

(52) U.S. Cl.
CPC ............ *C07D 223/16* (2013.01); *C07C 51/09* (2013.01); *C07C 51/367* (2013.01); *C07C 67/31* (2013.01); *C07C 303/40* (2013.01); *C07C 311/21* (2013.01); *C07D 301/00* (2013.01)

(58) Field of Classification Search
CPC ............................ C07D 223/16; C07C 311/21
USPC .......................................... 540/593; 564/84
See application file for complete search history.

(56) References Cited

U.S. PATENT DOCUMENTS

| | | |
|---|---|---|
| 2005/0004103 A1 | 1/2005 | Koshio et al. |
| 2006/0122170 A1 | 6/2006 | Koshio et al. |
| 2007/0244095 A1 | 10/2007 | Chen et al. |

FOREIGN PATENT DOCUMENTS

| | | |
|---|---|---|
| JP | 2006-151956 | 6/2006 |
| JP | 2006-151957 | 6/2006 |
| JP | 2008-504277 | 2/2008 |
| WO | WO 03/042181 | 5/2003 |
| WO | WO 2004/096775 | 11/2004 |

OTHER PUBLICATIONS

Li et al., Stereoselective Synthesis of Fluorinated 2,3-Dihydroquinolin-4(1H)-ones via a One-Pot Multistep Transformation, The Journal of Organic Chemistry, vol. 77, No. 5, pp. 2398-2406, Feb. 13, 2012.*
Supplementary European Search Report from the European Patent Office in counterpart European Application No. 13804693.3, dated Nov. 9, 2015.
Tomoichi Shinohara et al"Practical Stereoselective Synthesis of (2,3,4,5-Tetrahydro-1H-Benzo[b]azepin-5-yl)acetic Acid"; Chirality, vol. 12, pp. 425-430 (2000).
Issel Tsukamoto et al."Synthesis and structure-activity relationships of amide derivatives of (4,4-difluoro-1,2,3,4-tetrahydro-5H-1-benzazepin-5-ylidene) acetic acid as selective arginine vasopressin $V_2$ receptor agonists". Bioorganic & Medicinal Chemistry,vol. 17, pp. 3130-3141 (2009).
H. Furushio, JIPII Journal of Technical Disclosure No. 2004-504305, Yamanouchi Pharmaceutical CO., Ltd., Jun. 30, 2004, 13 pages.
K. Kondo et al., "7-Chloro-5-hydroxy-1-[2-methyl-4-(2-methylbenzoyl-amino)benzoyl]-2,3,4,5-tetrahydro-1H-1-benzazepine (OPC-41061): A Potent, Orally Active Nonpeptide Arginine Vasopressin $V_2$ Receptor Antagonist", *Bioorganic & Medicinal Chemistry*, (1999), vol. 7, No. 8, pp. 1743-1754.
A. Nishiguchi et al., "Preparation of a 1-unsubstituted-2,3-dihydro-1-benzazepine derivative", *Heterocycles*, (2007), vol. 71, No. 5, pp. 1183-1192.
Dai 22 Kai Abstracts Symposium on Progress in Organic Reactions and Synthesis, (1996), pp, 6 pages,
K. Suzuki et al., JIPII Journal of Technical Disclosure No. 98-6263, Yamanouchi Pharmaceutical CO., Ltd., Sep. 16, 1998, 6 pages.
K. Suzuki et al., JIPII Journal of Technical Disclosure No. 97-9952, Yamanouchi Pharmaceutical CO., Ltd., Dec. 15, 1997, 8 pages.
International Search Report from the Japanese Patent Office in International Application No. PCT/JP2013/066076, 16 pages, mailed Jul. 30, 2013.

* cited by examiner

*Primary Examiner* — Brenda Coleman
(74) *Attorney, Agent, or Firm* — Foley & Lardner LLP

(57) ABSTRACT

The present invention provides a method for producing a 4,4,7-trifluoro-1,2,3,4-tetrahydro-5H-1-benzazepine compound which has an superior agonistic activity to an arginine vasopressin V2 receptor and is useful as an active ingredient for a pharmaceutical composition for preventing and/or treating urinary frequency, urinary incontinence, enuresis, central diabetes insipidus, nocturia, nocturnal enuresis, or the like; and useful intermediates for use in the methods. The production method of the present invention is suitable for the industrial production of a medicament, because of a smaller number of steps, a higher yield, and a lower cost, as compared with the methods in the related art.

16 Claims, 2 Drawing Sheets

METHOD FOR PRODUCING 4,4,7-TRIFLUORO-1,2,3,4-TETRAHYDRO-5H-1-BENZAZEPINE COMPOUND AND INTERMEDIATE USED IN THE METHOD

CROSS-REFERENCE TO RELATED APPLICATIONS

This application is a national phase application of International Application No. PCT/JP2013/066076, filed Jun. 11, 2013, and claims priority of Japanese Patent Application No. JP 2012-131504, filed Jun. 11, 2012, the content of both of which is incorporated herein by reference.

TECHNICAL FIELD

The present invention relates to methods for producing (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (hereinafter referred to as "compound of the formula (1)" in some cases), and synthetic intermediates used in the methods.

BACKGROUND ART

It has been reported that the compound of the formula (1) has a superior agonistic activity to an arginine vasopressin V2 receptor and is useful as an active ingredient of a pharmaceutical composition for preventing and/or treating urinary frequency, urinary incontinence, enuresis, central diabetes insipidus, nocturia, nocturnal enuresis, or the like (Patent Document 1).

[Chem. 1]

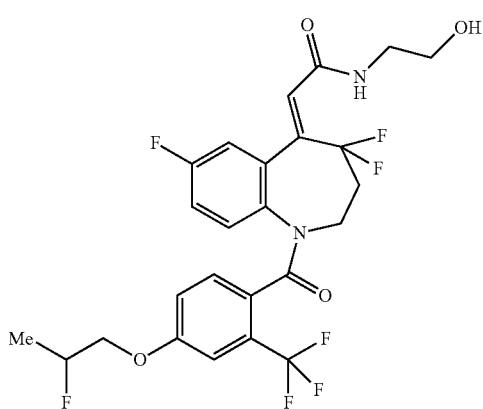

In reference to reference examples and examples described in Patent Document 1, the method for producing a compound of the formula (1) (Example 55) described therein is found to be those shown in the reaction scheme (I).

Further, with regard to a method for producing a compound of the formula (8-M) from a compound of the formula (16) through the steps 10 to 15 shown in the reaction scheme (I), the method is specifically described in Non-Patent Document 1.

Reaction scheme (I)

[Chem. 2]

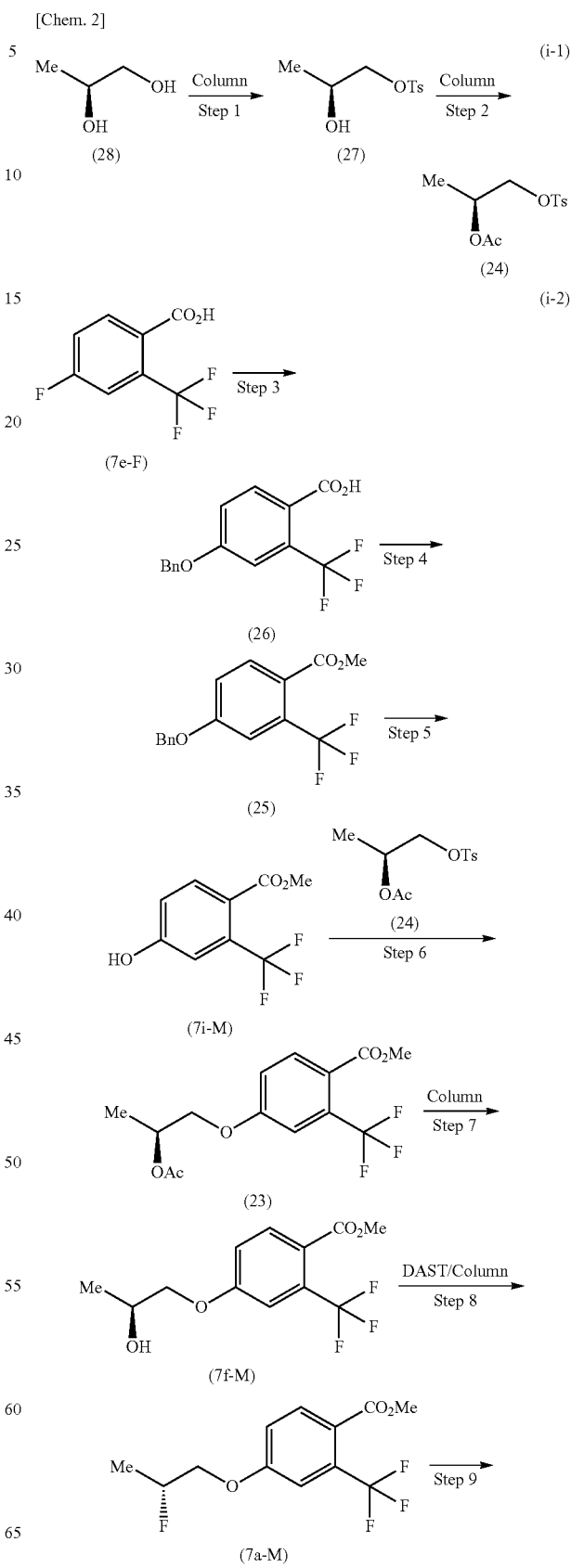

[Chem. 3]

(ii)

Step 10: (16) + (22) → (21)
Step 11: (21) → (20)
Step 12: (20) → (12)
Step 13: (12) → (11)
Step 14: (11) → (9-S)

[Chem. 4]

(iii)

Step 15: (9-S) → (8-M)
Step 16: (8-M) + (7) → (6-M)
Step 17: (6-M) → (5)
Step 18: (5) + (2) [EDC] →

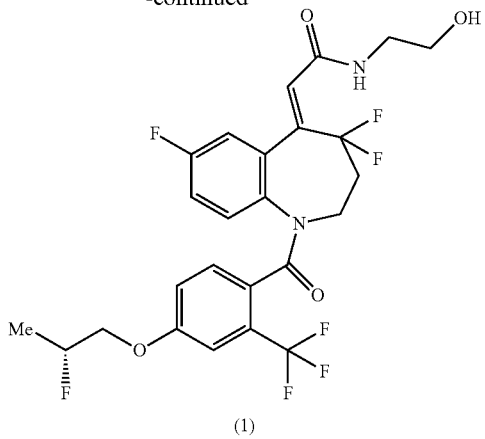

(1)

(in the formula, Ts represents p-toluenesulfonyl, Bn represents benzyl, Ac represents acetyl, Me represents methyl, DAST represents (diethylamino)sulfur trifluoride, and EDC represents 1-ethyl-3-(3-dimethylaminopropyl)carbodiimide hydrochloride).

However, the method for producing a compound of the formula (1) disclosed in Patent Document 1 requires a large number of steps, that is, eighteen steps in total, and includes, for example, a step with a low yield of products as described later, such as a step with a yield of about 30% or less, and thus, the overall yield from the compound of the formula (16) to the compound of the formula (1) as a final target is about 6%. In this regard, since the method has a big challenge in a yield and cost, from an industrial point of view, it was not entirely satisfactory production methods. In addition, the production method still needs to be further improved in terms of industrial production of a medicament from the viewpoint that the method includes a step (i.e. step 8 in the reaction scheme (I)) using (diethylamino)sulfur trifluoride (DAST) which is a nucleophilic fluorinating agent that is not easily handled due to its toxicity, corrosiveness, explosion hazard during a reaction, or the like, a step (i.e. step 18 in the reaction scheme (I)) using 1-ethyl-3-(3-dimethylaminopropyl)carbodiimide hydrochloride (EDC) which exhibits mutagenicity, and steps (i.e. steps 1, 2, 7, and 8 in the reaction scheme (I)) requiring purification by column chromatography.

RELATED ART

Patent Document

[Patent Document 1] Pamphlet of WO2004/096775
[Non-Patent Document 1] JIPII Journal of technical disclosure No. 2004-504305

DISCLOSURE OF INVENTION

Problems to be Solved by the Invention

The present invention has an object to provide production methods of a compound of the formula (1), which are suitable for industrial production of a medicament because of a smaller number of steps, a higher yield and a lower cost, as compared with the methods in the related art, and also provide useful synthetic intermediates for use in the methods.

Means for Solving the Problems

The present inventors have conducted extensive studies on methods for industrial production of the compound of the formula (1), and as a result, they have found improved methods as shown below:

(i) a method for producing the compound of the formula (7) efficiently in an extremely small steps without a step using DAST having a concern about safety, and further without steps requiring purification by column chromatography, by using appropriate starting materials and synthetic intermediates, (ii) a method for producing a compound of the formula (8) in a high yield by a reaction with an appropriate reagent, and/or (iii) a method for producing the compound of the formula (1) in a high yield without using EDC having a concern about toxicity.

They have found that the compound of the formula (1) can be produced by a method suitable for industrial production in a high yield and a low cost with use of one or more of these methods (i) to (iii), and in one embodiment, combining all of methods (i) to (iii), thereby they have completed the present invention.

That is, the present invention provides methods for producing the compound of the formula (1) shown below, and synthetic intermediates used in the methods.

[1]

A method for producing a compound of the formula (1) shown in the reaction scheme below, comprising:

a step of reacting a compound of the formula (5) with thionyl chloride (4) to produce a compound of the formula (3); and a step of amidating the compound of the formula (3) by reacting with 2-aminoethanol (2):

[Chem. 5]

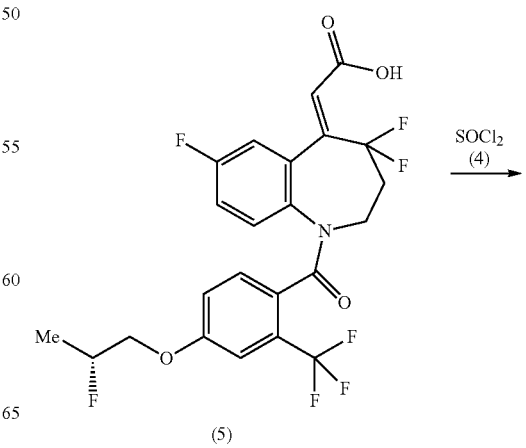

(5)

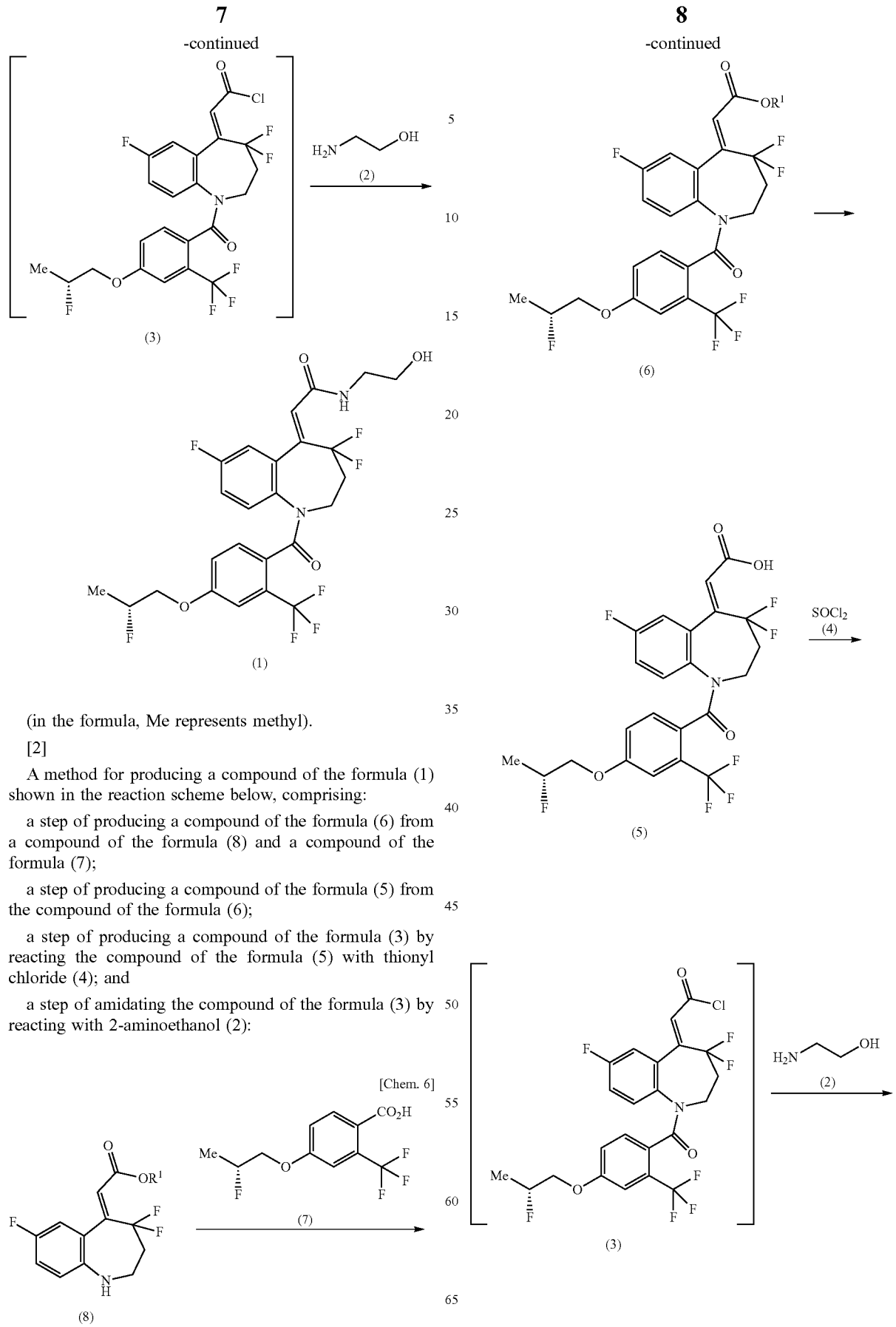

(in the formula, Me represents methyl).

[2]

A method for producing a compound of the formula (1) shown in the reaction scheme below, comprising:

a step of producing a compound of the formula (6) from a compound of the formula (8) and a compound of the formula (7);

a step of producing a compound of the formula (5) from the compound of the formula (6);

a step of producing a compound of the formula (3) by reacting the compound of the formula (5) with thionyl chloride (4); and a step of amidating the compound of the formula (3) by reacting with 2-aminoethanol (2):

-continued

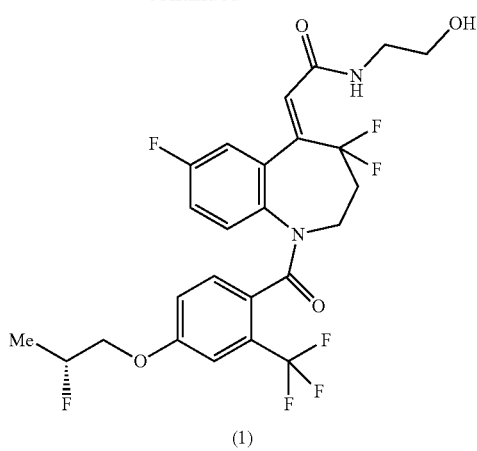 [SMILES: C[C@@H](F)COc1ccc(C(=O)N2CCC(F)(F)/C(=C\C(=O)NCCO)c3cc(F)ccc32)c(C(F)(F)F)c1]

(in the formula, R¹ represents lower alkyl, and Me represents methyl).

[3]

The method for producing the compound of the formula (1) described in [2] above, using the compound of the formula (8) produced by:

(X-1) a method for producing the compound of the formula (8) shown in the reaction scheme below, consisting of:
  a step of producing a compound of the formula (9) from a compound of the formula (11) and diphenylphosphonoacetic acid (10), and
  a step of producing the compound of the formula (8) from the compound of the formula (9):

[Chem. 7]

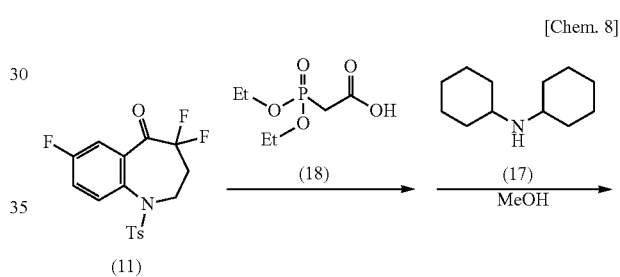

-continued

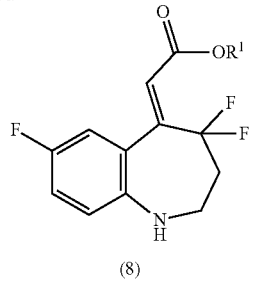

(in the formula, Ts represents p-toluenesulfonyl, Ph represents phenyl, and R¹ represents lower alkyl); or (X-2) a method for producing the compound of the formula (8) shown in the reaction scheme below, consisting of:
  a step of producing a compound of the formula (9-S) by reacting a compound of the formula (11) with diethylphosphonoacetic acid (18), and treating the obtained crude product with dicyclohexylamine (17) in methanol, and
  a step of producing the compound of the formula (8) from the compound of the formula (9-S):

[Chem. 8]

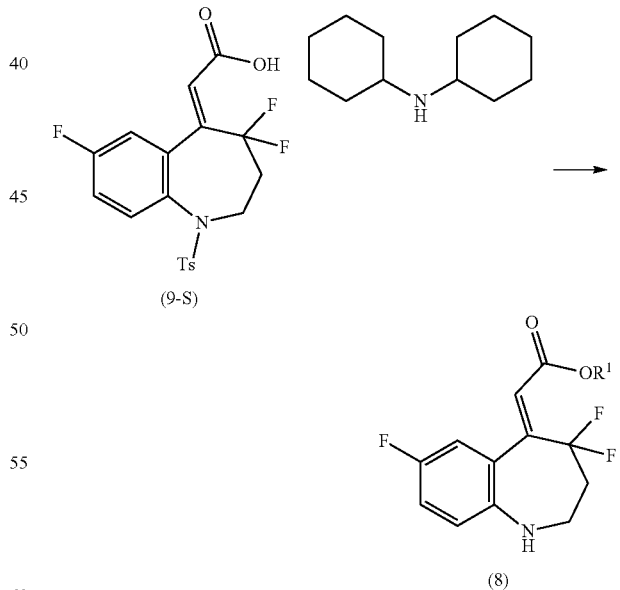

(in the formula, Ts represents p-toluenesulfonyl, Et represents ethyl, and R¹ represents lower alkyl).

[4]

The method for producing the compound of the formula (1) described in [3] above, using the compound of the formula (11) produced by:

(Y-1) a method for producing the compound of the formula (11) shown in the reaction scheme below, consisting of:
  a step of producing a compound of the formula (14) from a compound of the formula (16) and methyl 4-chlorobutyrate (15),
  a step of producing a compound of the formula (13) from the compound of the formula (14),
  a step of producing a compound of the formula (12) from the compound of the formula (13), and
  a step of producing the compound of the formula (11) from the compound of the formula (12):

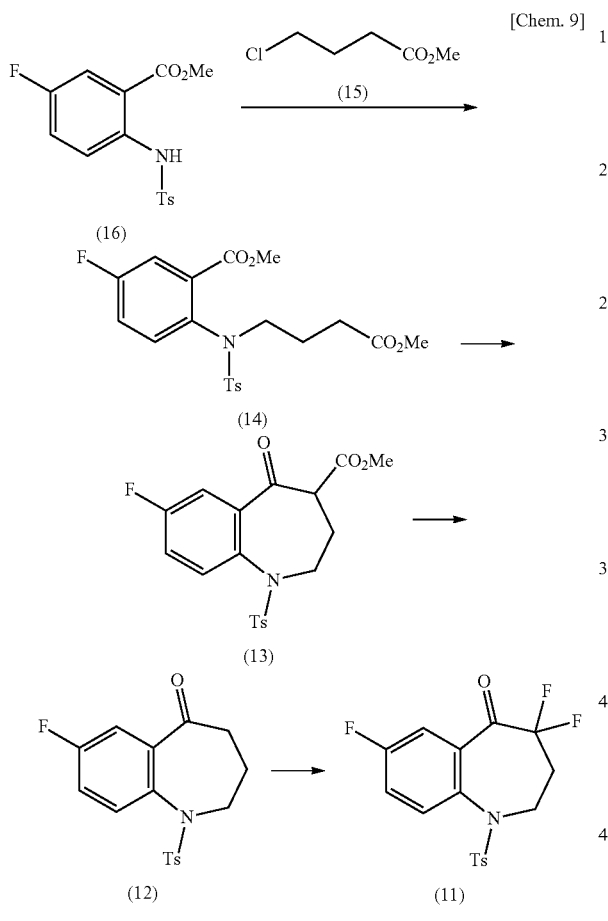

(in the formula, Ts represents p-toluenesulfonyl and Me represents methyl).

[5] The method for producing the compound of the formula (1) described in [4] above, wherein in the production method (Y-1), the compound of the formula (13) is produced without isolating the compound of the formula (14), and the compound of the formula (12) is produced without isolating the compound of the formula (13).

[6] The method for producing the compound of the formula (1) described in [2] to [5] above, using the compound of the formula (7) produced by any one of:
  (Z-1) a method for producing the compound of the formula (7) shown in the reaction scheme below, consisting of:
    a step of producing a compound of the formula (7a) from a compound of the formula (7c) and (2R)-2-fluoropropanol (7b), and
    a step of producing the compound of the formula (7) from the compound of the formula (7a):

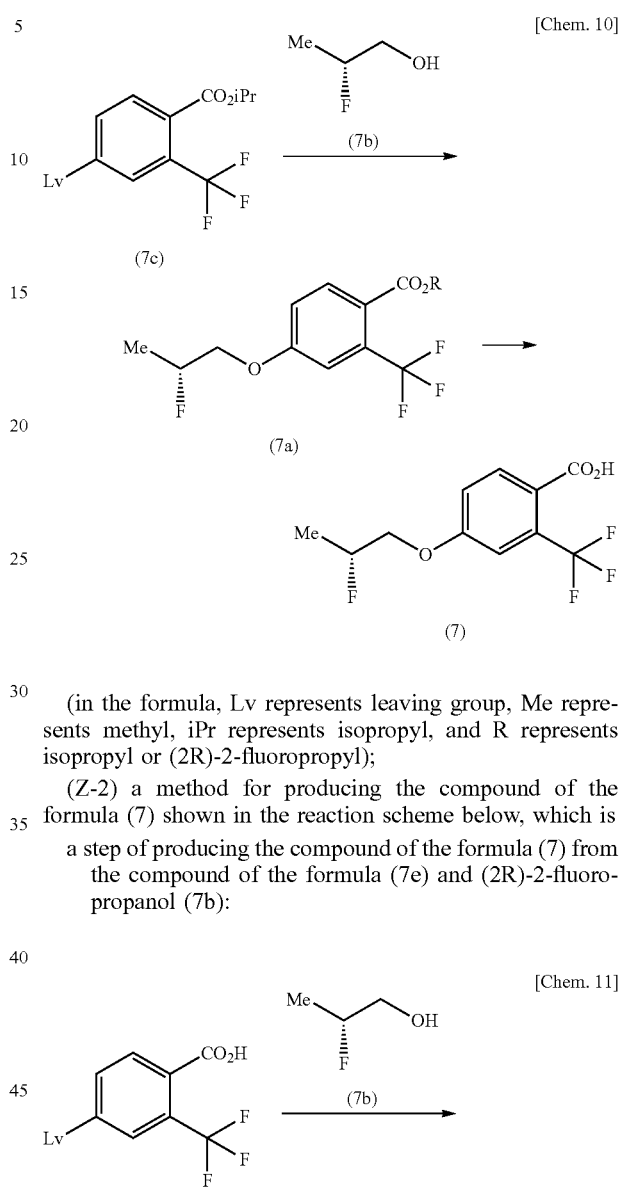

(in the formula, Lv represents leaving group, Me represents methyl, iPr represents isopropyl, and R represents isopropyl or (2R)-2-fluoropropyl);

(Z-2) a method for producing the compound of the formula (7) shown in the reaction scheme below, which is
  a step of producing the compound of the formula (7) from the compound of the formula (7e) and (2R)-2-fluoropropanol (7b):

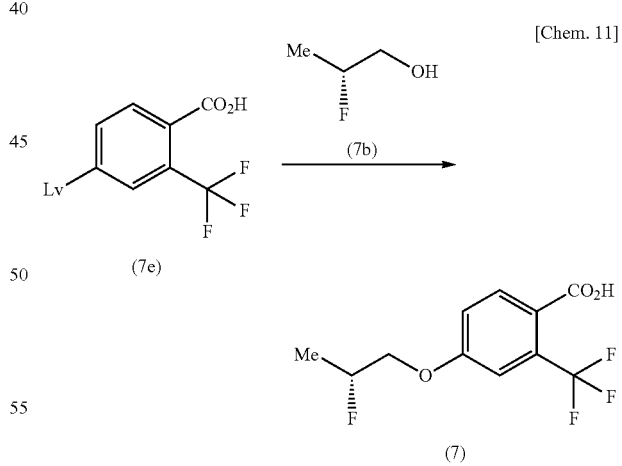

(in the formula, Lv represents a leaving group and Me represents methyl); or (Z-3) a method for producing the compound of the formula (7) shown in the reaction scheme below, consisting of:
  a step of producing a compound of the formula (7g) from a compound of the formula (7i) and (S)-glycidyl 3-nitrobenzenesulfonate (7h), a step of producing a compound of the formula (7f) by hydrogenation reaction of the compound of the formula (7g), and a step of producing the compound of the formula (7) from the compound of the formula (7f):

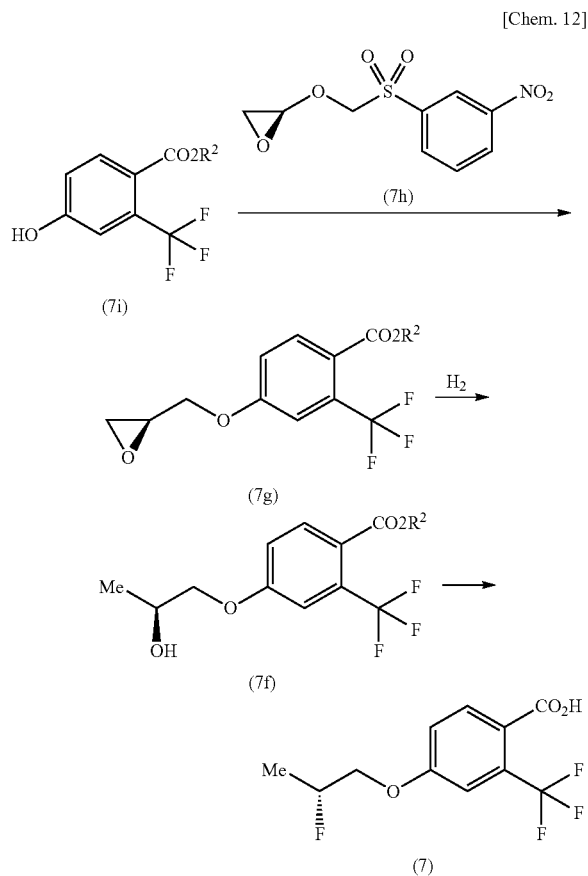

[Chem. 12]

(in the formula, $R^2$ represents lower alkyl and Me represents methyl).

[7]

The method for producing the compound of the formula (1) consisting of the method shown in (X-1) for producing the compound of the formula (8) described in [3] above, the method shown in (Z-1) for producing the compound of the formula (7) described in [6] above, and the production method described in [2] above.

[8]

The method for producing the compound of the formula (1) consisting of the method shown in (X-2) for producing the compound of the formula (8) described in [3] above, the method shown in (Z-1) for producing the compound of the formula (7) described in [6] above, and the production method described in [2] above.

[9]

The method for producing the compound of the formula (1) consisting of the method shown in (X-1) for producing the compound of the formula (8) described in [3] above, the method shown in (Z-2) for producing the compound of the formula (7) described in [6] above, and the production method described in [2] above.

[10]

The method for producing the compound of the formula (1) consisting of the method shown in (X-2) for producing the compound of the formula (8) described in [3] above, the method shown in (Z-2) for producing the compound of the formula (7) described in [6] above, and the production method described in [2] above.

[11]

The method for producing the compound of the formula (1) consisting of the method shown in (X-1) for producing the compound of the formula (8) described in [3] above, the method shown in (Z-3) for producing the compound of the formula (7) described in [6] above, and the production method described in [2] above.

[12]

The method for producing the compound of the formula (1) consisting of the method shown in (X-2) for producing the compound of the formula (8) described in [3] above, the method shown in (Z-3) for producing the compound of the formula (7) described in [6] above, and the production method described in [2] above.

[13]

The method for producing the compound of the formula (1) consisting of the method shown in (Y-1) for producing the compound of the formula (11) described in [4] above and the production method described in any one of [7] to [12] above.

[14]

The method for producing the compound of the formula (1) consisting of the method shown in (Y-1) for producing the compound of the formula (11) described in [5] above and the production method described in any one of [7] to [12] above.

[15]

(2Z)-{4,4,7-Trifluoro-1-[4-{[(2R)-2-fluoropropyl]oxy}-2-(trifluoromethyl)benzoyl]-1,2,3,4-tetrahydro-5H-1-benzazepin-5-ylidene}acetyl chloride (compound of the formula (3)).

[16]

Methyl 5-fluoro-2-{(4-methoxy-4-oxobutyl)[(4-methylphenyl)sulfonyl]amino}benzoate (compound of the formula (14)).

And, the compound of the formula (3) and the compound of the formula (14) are both novel compounds and useful synthetic intermediates in the present invention.

Further, in the reaction schemes described in the present specification, a "leaving group" represented by "Lv" is a commonly-used leaving group, such as fluoro, chloro, methanesulfonyloxy, p-toluenesulfonyloxy, and trifluoromethanesulfonyloxy; in one embodiment, fluoro, chloro, or methanesulfonyloxy; in another embodiment, fluoro or chloro; and in still another embodiment, fluoro. Further, the "lower alkyl" represented by $R^1$ and $R^2$ is a linear or branched alkyl having 1 to 6 carbon atoms, specifically, methyl, ethyl, propyl, isopropyl, butyl, isobutyl, tert-butyl, pentyl, or the like; in one embodiment, methyl or ethyl; and in another embodiment, methyl.

The present invention includes not only the compounds but also salts thereof described in the reaction schemes (II) (i) to (iii) below, and also synthetic methods using them. In one embodiment of such salts, specific examples thereof include acid addition salts with inorganic acids such as hydrochloric acid, hydrobromic acid, hydroiodic acid, sulfuric acid, nitric acid, phosphoric acid, and the like; acid addition salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like; salts with inorganic bases containing metals such as sodium, potassium, calcium, magnesium and the like or organic bases such as methylamine, ethylamine, ethanolamine, lysine, ornithine and dicyclohexylamine and the like; and ammonium salts and the like.

Furthermore, the present invention further includes various hydrates, solvates, and polymorphic crystal substances of the compounds and salts thereof described in the reaction schemes (II) (i) to (iii) below, and also synthetic methods using them. In addition, the present invention also includes compounds labeled with various radioactive or non-radioactive isotopes, and synthetic methods using them.

Effects of the Invention

The production method of the present invention has a smaller number of steps, a higher yield and a lower cost as compared with the methods in the related art, and can be suitably employed for industrial production of the compound of the formula (1) as a medicament. Further, the synthetic intermediates in the present invention are useful as intermediates for use in the synthetic methods of the present invention.

EMBODIMENTS FOR CARRYING OUT THE INVENTION

Figure 1:
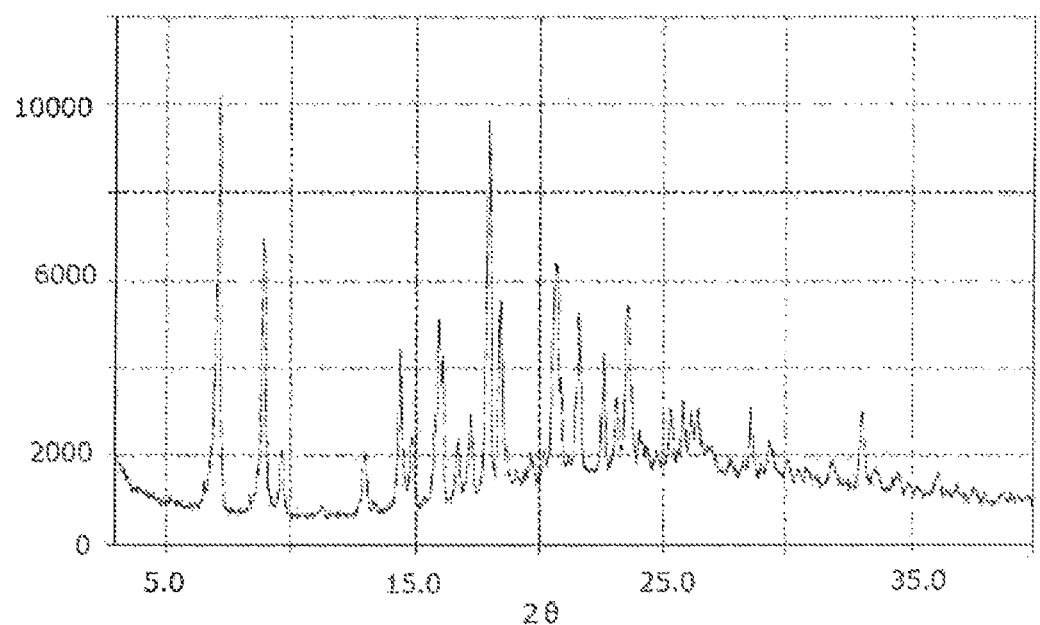
FIG. 1 shows an X-ray powder diffraction pattern of α type crystal of the compound of the formula (1) produced in Example 1.

A method for producing a 4,4,7-trifluoro-1,2,3,4-tetrahydro-5H-1-benzazepine compound of the present invention (steps 1 to 12) is shown in reaction scheme (II), and one embodiment of each step will be described below in the order from the step 1 to the step 12. Further, the compound of the formula (16) can be produced by the method described in Non-Patent Document 1, and other starting material compounds can also be produced by a method which is apparent to a person skilled in the art.

Reaction scheme (II)

[Chem. 13]

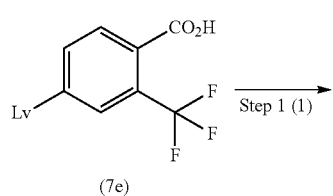

(7e)

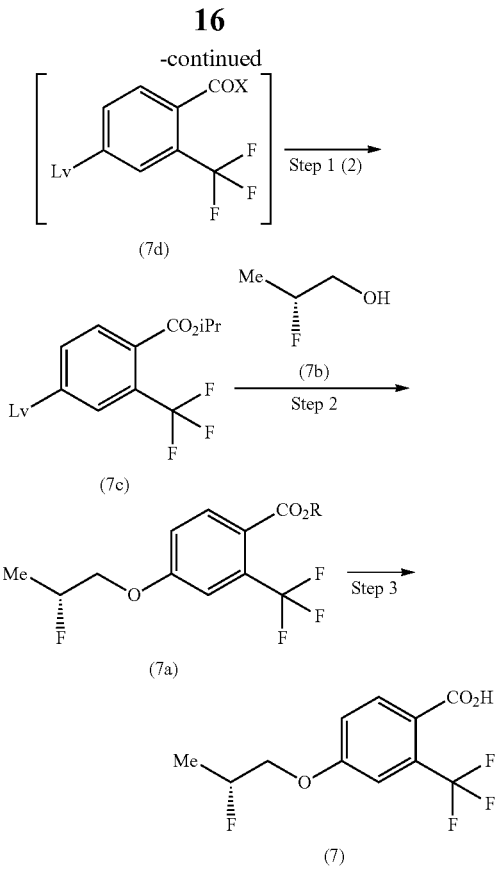

[Chem. 14]

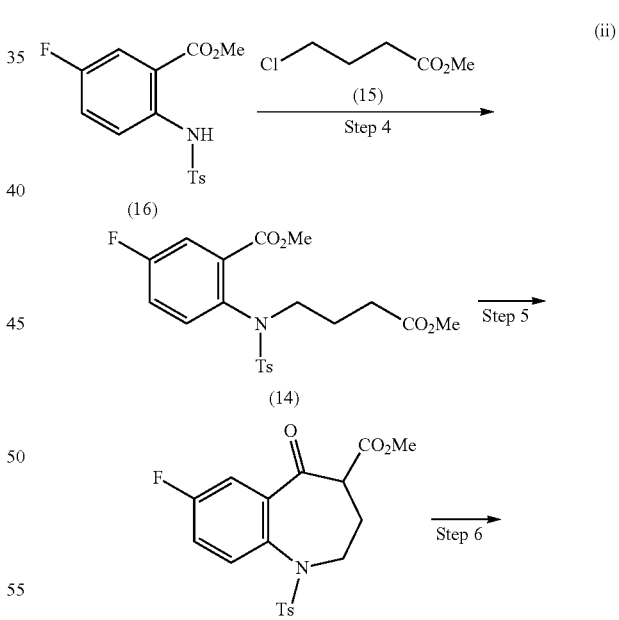

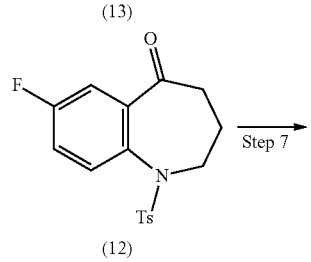

(12)

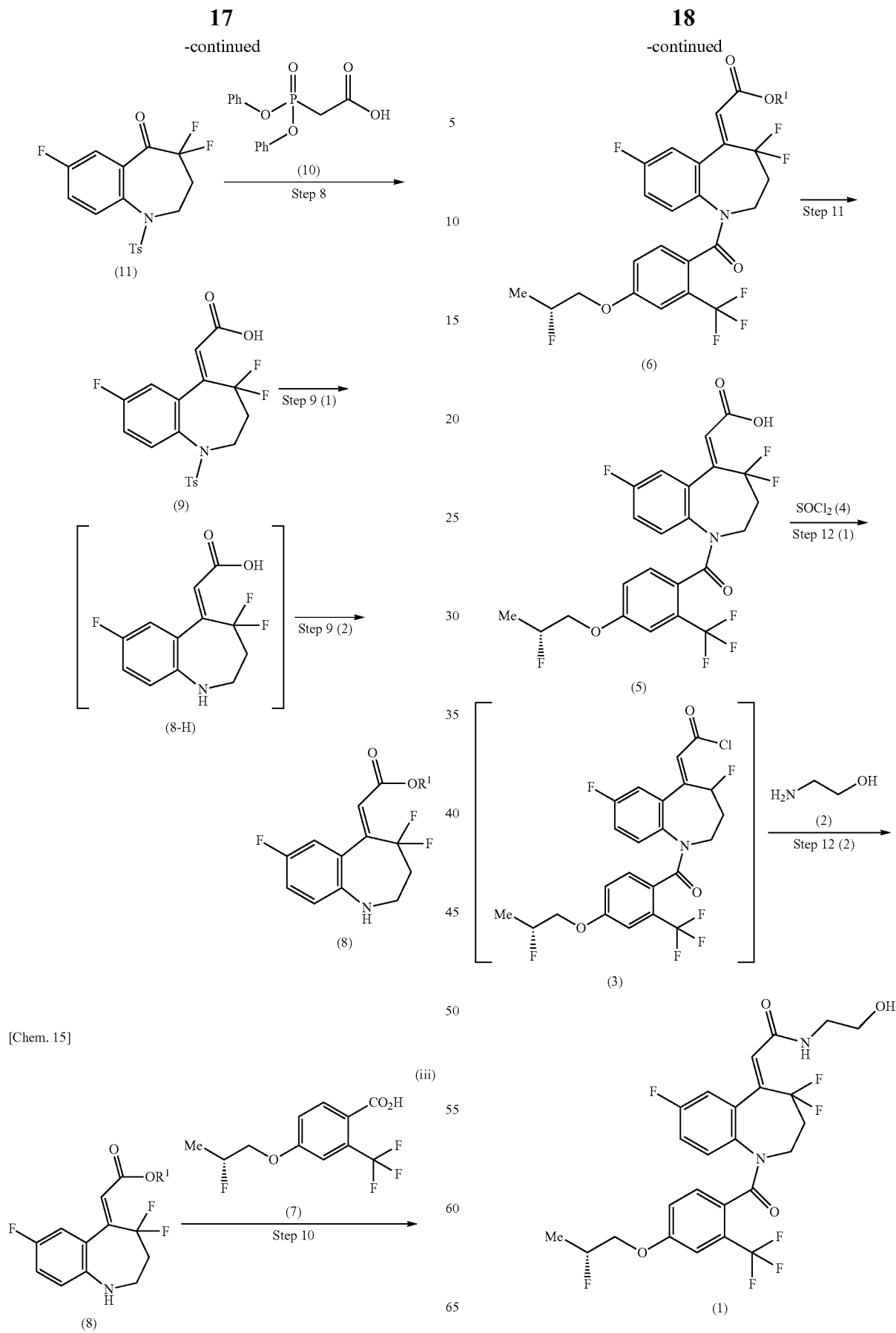

(in the formula, Lv represents a leaving group, X represents halogen, iPr represents isopropyl, Me represents methyl, R represents isopropyl or (2R)-2-fluoropropyl, Ts represents p-toluenesulfonyl, Ph represents phenyl, and $R^1$ represents lower alkyl).

Step 1

The step 1 shown in the reaction scheme (II) (i) is a step in which a compound of the formula (7e) is reacted with a halogenating agent to produce an acid halide of the formula (7d). Then, without isolation of the obtained acid halide, the acid halide is reacted with 2-propanol in the presence of a suitable base to produce an isopropyl ester of the formula (7c). Here, the halogenating agent in the step 1 (1) is not particularly limited, but examples thereof include phosphorous oxychloride, thionyl chloride, oxalyl dichloride, and the like. The reaction can be carried out under any temperature condition from cooling to heating, and preferably at −20° C. to 60° C. in a solvent which is inert to the reaction, such as halogenated hydrocarbons, aromatic hydrocarbons, ethers, and the like. And, the base used in the step 1 (2) is not particularly limited, but examples thereof include organic bases such as triethylamine, diisopropylethylamine, pyridine, and the like.

Step 2

The step 2 shown in the reaction scheme (II) (i) is a step in which a compound of the formula (7c) having a leaving group Lv is reacted with (2R)-2-fluoropropanol (7b) to produce a compound of the formula (7a) by an aromatic nucleophilic substitution reaction.

In the reaction of the present step, a compound of the formula (7c) and (2R)-2-fluoropropanol (7b) are used in equivalent amounts, or either thereof in an excess amount, and a mixture thereof is stirred under any temperature condition from cooling to heating and refluxing, and preferably at 0° C. to 80° C., usually for 0.1 hours to 5 days, in a solvent which is inert to the reaction or without a solvent, and in the presence of a suitable base. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. Here, examples of the base include organic bases such as triethylamine, N,N-diisopropylethylamine, N-methylmorpholine, and the like, or inorganic bases such as potassium carbonate, sodium carbonate, cesium carbonate, potassium tert-butoxide, sodium hydride, potassium hydroxide, and the like; but in one embodiment, inorganic bases; in another embodiment, cesium carbonate, sodium hydride, or potassium tert-butoxide; and in still another embodiment, potassium tert-butoxide.

Furthermore, in the aromatic nucleophilic substitution reaction of the step 2, the reaction time varies depending on the base used, e.g. as in "(alternative method for step 2 of Example 1)" described in Example 2 below, when cesium carbonate is used, it takes about 27 hours at 25° C. to 50° C. until the completion of the reaction, but when potassium tert-butoxide is used as in "(steps 1 to 3)" described in Example 1, the reaction is completed in 5 hours at 0° C., and thus, the reaction time can be reduced.

Step 3

The step 3 shown in the reaction scheme (II) (i) is a step in which the compound of the formula (7a) is hydrolyzed to produce a compound of the formula (7).

The hydrolysis reaction can be carried out, for example, with reference to "Protective Groups in Organic Synthesis", Greene and Wuts, 4$^{th}$ edition, John Wiley & Sons Inc., 2006.

Step 4

The step 4 shown in the reaction scheme (II) (ii) is a step in which a compound of the formula (16) is reacted with methyl 4-chlorobutyrate (15) to produce a compound of the formula (14).

In this reaction, the compound of the formula (16) and methyl 4-chlorobutyrate (15) are used in equivalent amounts, or either thereof in an excess amount, and a mixture thereof is stirred under any temperature condition from cooling to heating and refluxing, and preferably at 0° C. to 80° C., usually for 0.1 hours to 5 days, in a solvent which is inert to the reaction, and in the presence of a base. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. Examples of the base include organic bases such as triethylamine, diisopropylethylamine, 1,8-diazabicyclo[5.4.0]-7-undecene, n-butyllithium, and the like, or inorganic bases such as sodium carbonate, potassium carbonate, sodium hydride, potassium tert-butoxide, and the like. Further, it may be advantageous in some cases to carry out the reaction in the presence of iodides such as potassium iodide.

Step 5

The step 5 shown in the reaction scheme (II) (ii) is a step in which a compound of the formula (14) is reacted in the presence of a suitable base to produce a compound of the formula (13).

In this reaction, the compound of the formula (14) is stirred under any temperature condition from cooling to heating and refluxing, and preferably at −20° C. to 80° C., usually for 0.1 hours to 5 days, in a solvent which is inert to the reaction, and in the presence of a base. Examples of the solvent used herein are not particularly limited, but include aromatic hydrocarbons such as benzene, toluene, xylene, and the like, ethers such as diethyl ether, tetrahydrofuran, dioxane, and dimethoxyethane, halogenated hydrocarbons such as dichloromethane, 1,2-dichloroethane, chloroform, and the like, N,N-dimethylformamide, and a mixture thereof. Examples of the base include organic bases such as triethylamine, diisopropylethylamine, 1,8-diazabicyclo[5.4.0]-7-undecene, and the like, or inorganic bases such as sodium carbonate, potassium carbonate, sodium hydride, potassium tert-butoxide, and the like.

Step 6

The step 6 shown in the reaction scheme (II) (ii) is a step in which a compound of the formula (13) is heated to produce a compound of the formula (12) by a Krapcho decarboxylation reaction.

In this reaction, the compound of the formula (13) is stirred under heating, usually for 0.1 hours to 5 days in a solvent which is inert to the reaction. Examples of the solvent used herein include N,N-dimethylformamide, dimethylsulfoxide, water, and the like. Further, it may be advantageous to carry out the reaction in the presence of chlorides such as lithium chloride cyanides and the like, or in the presence of cyanides such as potassium cyanide and the like.

Step 7

The step 7 shown in the reaction scheme (II) (ii) is a step in which the compound of the formula (12) is reacted with an electrophilic fluorinating agent to produce a compound of the formula (11).

In this reaction, the compound of the formula (12) is stirred under any temperature condition from cooling to heating and refluxing, and preferably at room temperature to 100° C., usually for 0.1 hours to 5 days, in a solvent which is inert to the reaction. Here, examples of the electrophilic fluorinating agent include N,N'-difluoro-2,2'-bipyridinium bis(tetrafluoroborate), 2,6-dichloro-1-fluoropyridinium tetrafluoroborate, 1-fluoro-2,4,6-trimethylpyridinium tetrafluoroborate, and the like. Examples of the solvent used herein include acetonitrile, acetate, formic acid, and the like. Further, it may be advantageous in some cases to carry out the reaction of the compound of the formula (12) in the presence of an acid. In addition, it may be advantageous in some cases to carry out the reaction of the compound of the formula (12) in the presence of a catalytic amount of sodium trifluoromethanesulfonate.

Step 8

The step 8 shown in the reaction scheme (II) (ii) is a step in which a compound of the formula (9) is produced from the compound of the formula (11) by a Horner-Wadsworth-Emmons reaction.

Here, by using diphenylphosphonoacetic acid (10) as a reagent for a Horner-Wadsworth-Emmons reaction, the reaction proceeds with high Z selectivity, and the compound of the formula (9) can be produced efficiently.

In this reaction, a mixture of the compound of the formula (11) and diphenylphosphonoacetic acid (10) is stirred under any temperature condition from cooling to room temperature, and preferably −78° C. to 0° C., usually for 0.1 hours to 5 days, in a solvent which is inert to the reaction, and in the presence of a suitable base. Here, examples of the base include 1,8-diazabicyclo[5.4.0]-7-undecene, sodium hydride, sodium hexamethyldisilazide, potassium hexamethyldisilazide, benzyltrimethyl ammonium hydroxide, and the like, in one embodiment, 1,8-diazabicyclo[5.4.0]-7-undecene, sodium hydride, and sodium hexamethyldisilazide, and in another embodiment, sodium hexamethyldisilazide. Examples of the solvent used herein include aromatic hydrocarbons such as benzene, toluene, xylene, and the like, ethers such as diethyl ether, tetrahydrofuran, dioxane, dimethoxyethane, and the like, and a mixture thereof, in one embodiment, toluene, diethyl ether, tetrahydrofuran, and dimethoxyethane, and in another embodiment, tetrahydrofuran.

Step 9

The step 9 shown in the reaction scheme (II) (ii) is a step in which the compound of the formula (9) is esterified after removal of a p-toluenesulfonyl group thereof to produce a compound of the formula (8). The step of removal of p-toluenesulfonyl group shown in the step 9 (1) and the esterification reaction shown in the step 9 (2) can be carried out with reference to "Protective Groups in Organic Synthesis", Greene and Wuts, 3$^{rd}$ edition, John Wiley & Sons Inc., 1999 as described above.

Step 10

The step 10 shown in the reaction scheme (II) (iii) is a step in which the carboxylic acid compound of the formula (7) is converted to a reactive derivative and then amidated with the compound of the formula (8) to produce a compound of the formula (6). Examples of the reactive derivative of the carboxylic acid include acid halides which can be obtained by the reaction with a halogenating agent such as phosphorus oxychloride thionyl chloride, and the like, mixed acid anhydrides which can be obtained by the reaction with isobutyl chloroformate or the like, and active esters obtained by the condensation with 1-hydroxybenzotriazole or the like. The reaction of the reactive derivative and the compound of the formula (8) can be carried out under any temperature condition from cooling to heating, and preferably at −20° C. to 60° C., in a solvent which is inert to the reaction, such as halogenated hydrocarbons, aromatic hydrocarbons, and ethers.

Step 11

The step 11 shown in the reaction scheme (II) (iii) is a step in which a compound of the formula (5) is produced by a hydrolysis reaction of the compound of the formula (6).

The reaction condition is the same as that of the step 3 shown in the reaction scheme (II) (i).

Step 12

The step 12 shown in the reaction scheme (II) (iii) is a step in which the compound of the formula (5) is converted into the carboxylic acid chloride of the formula (3) using thionyl chloride (4), and then obtained compound of the formula (3) is reacted with 2-aminoethanol (2) in the presence of a suitable base to produce the compound of the formula (1).

This reaction is carried out under cooling, under any temperature condition from cooling to room temperature, or under any temperature condition from room temperature to heating, in an organic solvent which is inert to the reaction, such as halogenated hydrocarbons, aromatic hydrocarbons, ethers, esters, acetonitrile, N,N-dimethylformamide, and dimethylsulfoxide.

Further, it may be advantageous in some cases for the smooth progress of the reaction to carry out the reaction using an excess amount of 2-aminoethanol (2) or in the presence of a base such as N-methylmorpholine, trimethylamine, triethylamine, diisopropylethylamine, N,N-dimethylaniline, pyridine, 4-(N,N-dimethylamino)pyridine, picoline, and lutidine. Further, a salt of a weak base and a strong acid, such as pyridine hydrochloride, pyridine p-toluenesulfonate, N,N-dimethylaniline hydrochloride, and the like, may be used. The pyridine may be also used as a solvent.

In another embodiment of the production process of the present invention, other methods for producing the compound of the formula (7) in the reaction scheme (II) is specifically shown in the following reaction scheme (III).

Reaction scheme (III)

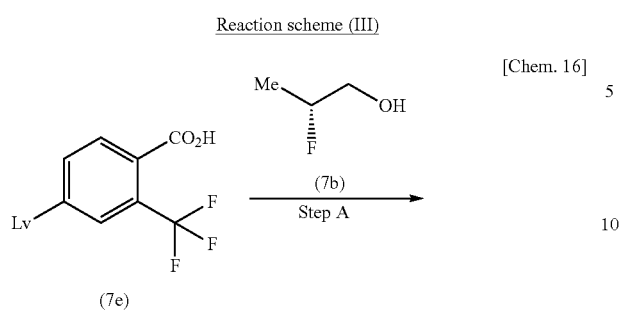

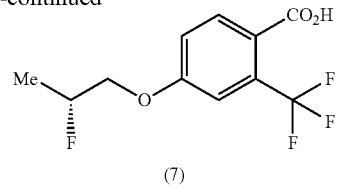

(in the formula, Lv represents a leaving group and Me represents methyl).

The step A is a step in which a compound of the formula (7e) is reacted with (2R)-2-fluoropropanol (7b) to produce the compound of the formula (7). The reaction condition is the same as that of the step 2 shown in the reaction scheme (II).

In another embodiment, another method for producing the compound of the formula (7) is specifically described in the following reaction scheme (IV).

Reaction scheme (IV)

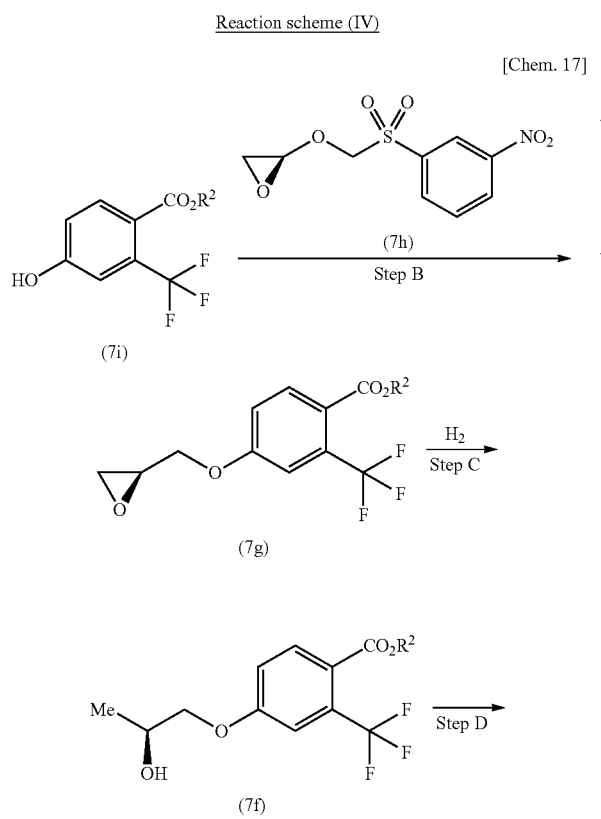

(in the formula, $R^2$ represents lower alkyl and Me represents methyl).

Step B

The step B is a step in which a compound of the formula (7i) is reacted with (S)-glycidyl 3-nitrobenzenesulfonate (7h) to produce a compound of (7g).

In this reaction, the compound of the formula (7i) and the (S)-glycidyl 3-nitrobenzenesulfonate (7h) are used in equivalent amounts, or either thereof in an excess amount, and a mixture thereof is stirred under any temperature condition from cooling to heating and refluxing, and preferably at 0° C. to 80° C., usually for 0.1 hours to 5 days, in a solvent which is inert to the reaction, and in the presence of a base. Examples of the solvent used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. Examples of the base include organic bases such as triethylamine, diisopropylethylamine, 1,8-diazabicyclo[5.4.0]-7-undecene, n-butyllithium, and the like, or inorganic bases such as sodium carbonate, potassium carbonate, sodium hydride, potassium tert-butoxide, and the like. Further, it may be advantageous in some cases to carry out the reaction in the presence of cesium fluoride.

Step C

The step C is a step in which a compound of (7f) is produced by hydrogenation of a compound of the formula (7g).

In this reaction, the compound of the formula (7g) is stirred, usually for 1 hour to 5 days, in a solvent which is inert to the reaction in the presence of a metal catalyst under a hydrogen atmosphere. This reaction is usually carried out under any temperature condition from cooling to heating, and preferably at room temperature. Examples of the solvent used herein are not particularly limited, but include alcohols such as methanol, ethanol, 2-propanol, and the like, ethers such as diethyl ether, tetrahydrofuran, dioxane, dimethoxyethane, and the like, water, ethyl acetate, N,N-dimethylformamide, dimethylsulfoxide, and a mixture thereof. As the metal catalyst, palladium catalysts such as palladium carbon, palladium black, palladium hydroxide, and the like, platinum catalysts such as a platinum plate, platinum oxide, and the like, nickel catalysts such as reduced nickel, Raney nickel, and the like, rhodium catalysts such as tristriphenylphosphine chlororhodium and the like, or iron catalysts such as reduced iron and the like are preferably used. Instead of the hydrogen gas, from an equivalent amount to an excess amount of formic acid or ammonium formate can also be used as a hydrogen source, relative to the compound of the formula (7g).

Step D

The step D is a step in which the compound of the formula (7f) is converted into the compound of the formula (7). The reaction condition is the same as that of the steps 8 and 9 shown in the reaction scheme (I) (i-2).

Alternative method (the steps E to F) for producing the compound of the formula (8) shown in the reaction scheme (II), which is another embodiment of the production process of the present invention, is specifically described in the following reaction scheme (V).

Reaction scheme (V)

[Chem. 18]

(in the formula, Ts represents p-toluenesulfonyl, the compound of the formula (19) having crosslinked double bonds represents a mixture of E-forms and Z-forms of the double bonds, and $R^1$ represents lower alkyl).

Step E-(1)

The step E-(1) shown in the reaction scheme (V) is a step in which a compound of the formula (19) is produced by a Horner-Wadsworth-Emmons reaction of the compound of the formula (11) and diethylphosphonoacetic acid (18). The present step can be carried out under the same reaction condition as the step 8 in the reaction scheme (II) (ii) except that the compound of the formula (18) is used instead of the compound of the formula (10).

Step E-(2)

The step E-(2) shown in the reaction scheme (V) is a step in which the compound of the formula (19) is reacted with dicyclohexylamine (17) in methanol to produce a dicyclohexylamine salt of the formula (9-S).

In this reaction, the compound of the formula (19) and dicyclohexylamine are used in equivalent amounts, or either thereof in an excess amount, and a mixture thereof is stirred under any temperature condition from cooling to heating and refluxing, and preferably at 0° C. to room temperature, usually for 0.1 hours to 5 days, in methanol, and the crystal of the formula (9-S) thus precipitated is collected by filtration.

Step F

The step F shown in the reaction scheme (V) is a step in which compound of the formula (8) is produced from the compound of the formula (9-S). The reaction condition can be carried out in the same manner as in the method for producing the compound of the formula (8-M) described in Non-Patent Document 1 (denoted as the compound [8] in the document).

As the compound of the formula (1), the following two types of polymorphic crystals exist, and thus, α type crystal of the compound of the formula (1) was acquired in Reference Example, and Examples 1 and 2 (alternative method 1 for step 12 of Example 1) and β type crystal of the compound of the formula (1) was acquired in Example 2 (alternative method 2 for step 12 of Example 1).

(α Type Crystal)

Figure 2:
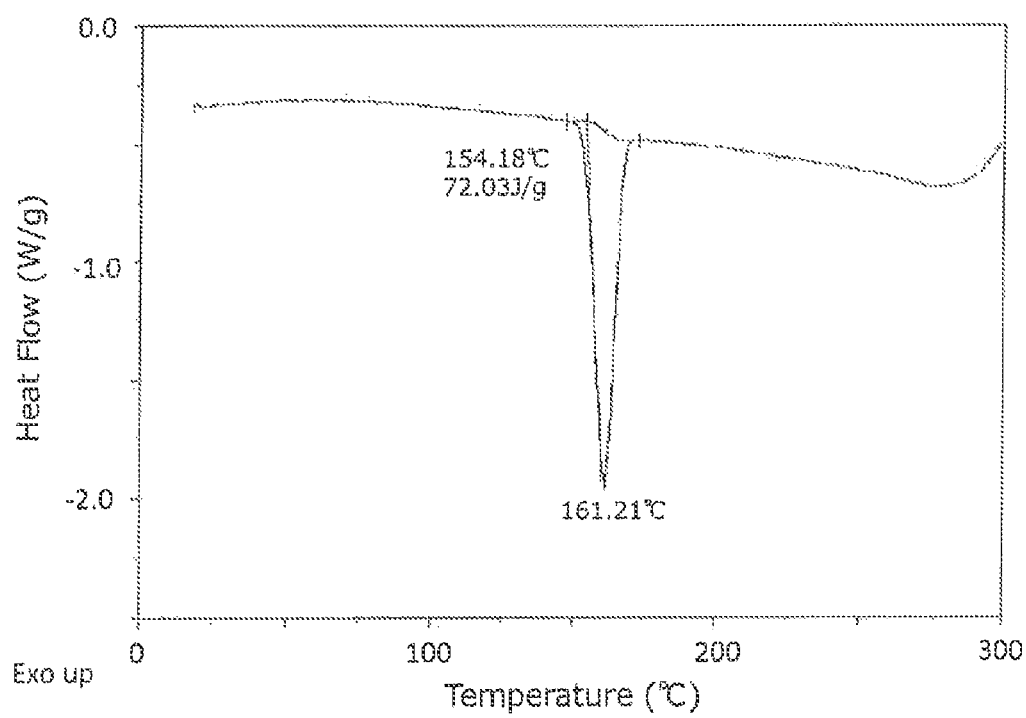
FIG. 2 shows a DSC chart of α type crystal of the compound of the formula (1) produced in Example 1.

The α type crystal is a crystal characterized by showing peaks at 2θ (°) of around 7.14, around 8.86, around 9.62, around 12.98, around 14.36, around 14.84, around 15.90, around 17.20, around 17.94, around 18.44, around 18.64, around 20.64, around 21.62, around 22.62, around 23.14, around 23.57, around 25.32, and around 25.84 in the X-ray powder diffraction using Cu as a radiation source, and in another embodiment, crystal further having a endothermic on-set temperature of around 154.18° C. in DSC. Further, the results of X-ray powder diffraction analysis and DSC analysis of the α type crystal obtained in Example 1 are shown in FIGS. 1 and 2, respectively. The crystal was stable under the preservation conditions of 40° C./75% RH for 3 months.

(β Type Crystal)

Figure 3:
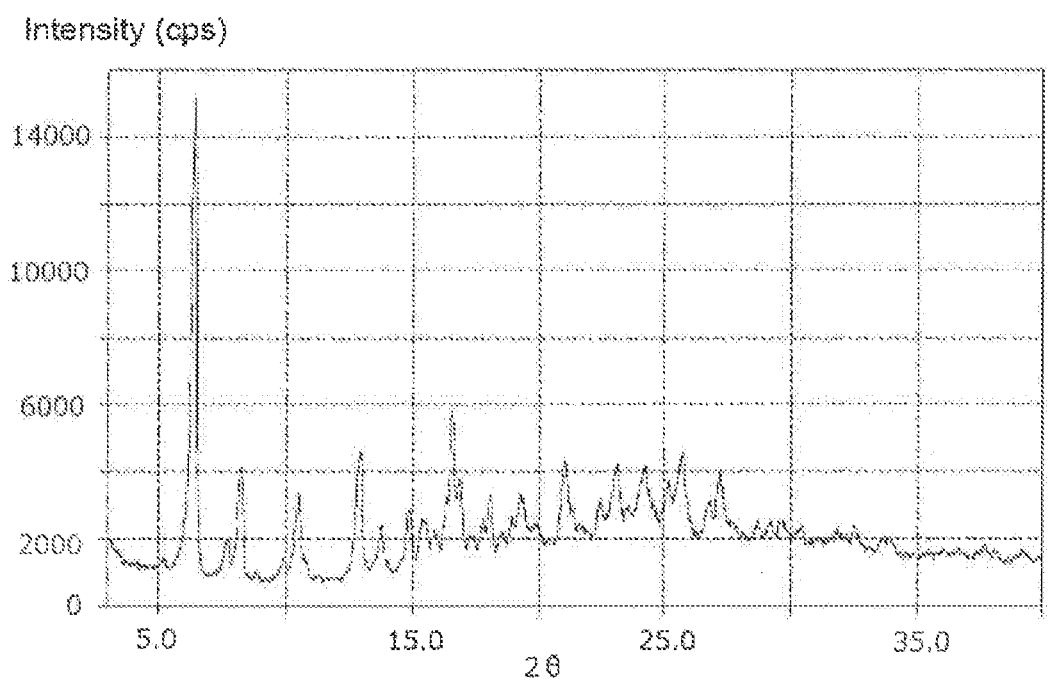
FIG. 3 shows an X-ray powder diffraction pattern of β type crystal of the compound of the formula (1) produced in Example 2 (alternative method 2 for step 12 of Example 1).
Figure 4:
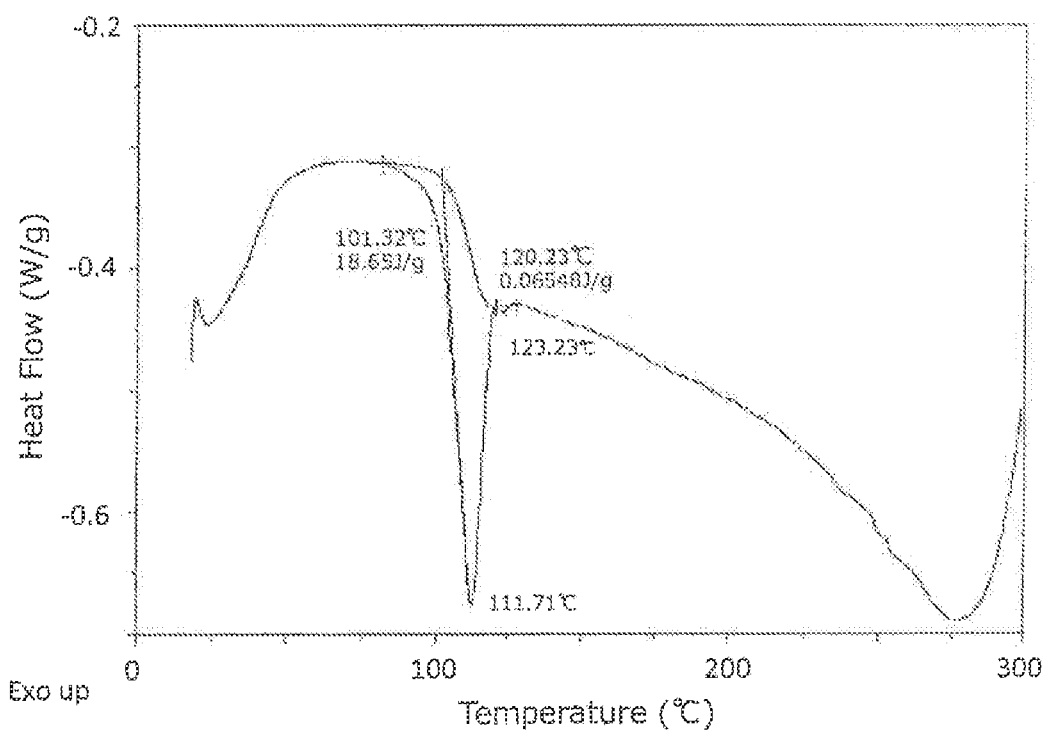
FIG. 4 shows a DSC chart of β type crystal of the compound of the formula (1) produced in Example 2 (alternative method 2 for step 12 of Example 1).

The β type crystal is a crystal characterized by showing peaks at 2θ (°) of around 6.44, around 8.26, around 10.44, around 12.88, around 13.72, around 14.82, around 16.50, around 20.92, around 23.16, around 25.74, and around 27.20 in the X-ray powder diffraction using Cu as a radiation source, and in another embodiment, crystal further having a endothermic on-set temperature of around 101.32° C. in DSC. Further, the results of X-ray powder analysis and DSC analysis of the β type crystal obtained in Example 2 (alternative method 2 for step 12 of Example 1) are shown in FIGS. 3 and 4, respectively.

Moreover, with the X-ray powder diffraction patterns, diffraction angles and overall patterns are important for identification of crystals in terms of the properties of the data, and since the relative intensity may vary slightly depending on the direction of crystal growth, the particle size, and the measurement conditions, it should not be strictly construed. Furthermore, the term "around" as used in the values of the diffraction angles (2θ) in the X-ray powder diffraction pattern means an approximate value, in one embodiment, it means a range of the value ±0.2°, and in still another embodiment, a range of the value ±0.1°. In addition, the term "around" as used in the value of the endothermic on-set temperature in DSC means a value of the temperature of the endothermic on-set (extrapolation initiation), in another embodiment, a range of the value ±2° C., and in still another embodiment, a range of the value ±1° C.

Next, the known method for producing a compound of the formula (1) shown in the reaction scheme (I) and the yield thereof are shown in Reference Example. Further, in the present specification, "$^1$H-NMR (CDCl$_3$)" represents δ (ppm) of a peak in $^1$H-NMR in deuterochloroform, "$^1$H-NMR (DMSO-d$_6$)" represents δ (ppm) of a peak in $^1$H-NMR in dimethylsulfoxide-d$_6$, "EI" represents EI-MS [M]$^+$, "FAB+" represents FAB-MS [M+H]$^+$, "ESI+" represents ESI-MS [M+H]$^+$, and "ESI−" represents ESI-MS [M−H]$^−$.

Reference Example

Step 1

Synthesis of (2S)-2-hydroxypropyl 4-methylbenzenesulfonate (compound of formula (27))

By the method described in Reference Example 30 of Patent Document 1, (2S)-2-hydroxypropyl-4-methylbenzenesulfonate was obtained in a yield of 48.4%. Further, in this step, silica gel column chromatography (hexane/ethyl acetate=3:1 to 1:1) was used for purification of the product.

$^1$H-NMR (CDCl$_3$): 1.16 (3H, d, J=6.8 Hz), 2.46 (3H, s), 3.83-4.00 (2H, m), 4.02-4.10 (1H, m), 7.36 (2H, d, J=8.0 Hz), 7.80 (2H, d, J=8.0 Hz)

FAB+: 231

Step 2

Synthesis of (2S)-1-{[(4-methylphenyl)sulfonyl]oxy}propan-2-yl acetate (compound of formula (24))

By the method described in Reference Example 30A of Patent Document 1, (2S)-1-{[(4-methylphenyl)sulfonyl]oxy}propan-2-yl acetate was obtained in a yield of 94.6%. Further, in this step, silica gel column chromatography (hexane/ethyl acetate=3:1) was used for purification of the product.

$^1$H-NMR (CDCl$_3$): 1.22 (3H, d, J=6.8 Hz), 1.97 (3H, s), 2.46 (3H, s), 4.00-4.08 (2H, m), 4.99-5.07 (1H, m), 7.36 (2H, d, J=8.3 Hz), 7.79 (2H, d, J=8.3 Hz)

FAB+: 273

Step 3

Synthesis of 4-(benzyloxy)-2-(trifluoromethyl)benzoic acid (Compound of the formula (26))

By the method described in Reference Example 1 of Patent Document 1, 4-(benzyloxy)-2-(trifluoromethyl)benzoic acid was obtained in a yield of 93.8%.

$^1$H-NMR (CDCl$_3$): 5.15 (2H, s), 7.14 (1H, dd, J=2.4, 8.8 Hz), 7.36-7.45 (6H, m), 8.05 (1H, d, J=8.8 Hz)

FAB+: 297

Steps 4 and 5 (Successive Steps)

Synthesis of methyl 4-hydroxy-2-(trifluoromethyl)benzoate (compound of formula (7i-M))

By the method described in Reference Example 26 of Patent Document 1, methyl 4-hydroxy-2-(trifluoromethyl)benzoate was obtained.

$^1$H-NMR (CDCl$_3$): 3.91 (3H, s), 5.45 (1H, s), 7.01 (1H, dd, J=2.8, 8.8 Hz), 7.21 (1H, d, J=2.8 Hz), 7.81 (1H, d, J=8.8 Hz)

FAB+: 221

Step 6

Synthesis of methyl 4-{[(2S)-2-acetoxypropyl]oxy}-2-(trifluoromethyl)benzoate (compound of formula (23))

By the method described in Reference Example 30B of Patent Document 1, methyl 4-{[(2S)-2-acetoxypropyl]oxy}-2-(trifluoromethyl)benzoate was obtained in an overall yield of three steps, the steps 4 to 6, of 65.6%.

$^1$H-NMR (CDCl$_3$): 1.38 (3H, d, J=6.9 Hz), 2.07 (3H, s), 3.91 (3H, s), 4.03-4.14 (2H, m), 4.94-5.05 (1H, m), 7.07 (1H, dd, J=2.5, 8.8 Hz), 7.25-7.29 (1H, m), 7.85 (1H, d, J=8.8 Hz)

FAB+: 321

Step 7

Synthesis of methyl 4-{[(2S)-2-hydroxypropyl]oxy}-2-(trifluoromethyl)benzoate (compound of formula (7f-M))

By the method described in Reference Example 31 of Patent Document 1, methyl 4-{[(2S)-2-hydroxypropyl]oxy}-2-(trifluoromethyl)benzoate was obtained in a yield of 82.6%. Further, in this step, silica gel column chromatography (hexane/ethyl acetate=3:1) was used for purification of the product.

$^1$H-NMR (CDCl$_3$): 1.38 (3H, d, J=7.0 Hz), 3.91 (3H, s), 3.99-4.04 (2H, m), 4.19-4.26 (1H, m), 7.08 (1H, dd, J=2.6, 8.8 Hz), 7.29 (1H, d, J=2.6 Hz), 7.86 (1H, d, J=8.8 Hz)

FAB+: 279

Step 8

Synthesis of methyl 4-{[(2R)-2-fluoropropyl]oxy}-2-(trifluoromethyl)benzoate (compound of formula (7a-M))

By the method described in Reference Example 32 of Patent Document 1, methyl 4-{[(2R)-2-fluoropropyl]oxy}-

2-(trifluoromethyl)benzoate was obtained in a yield of 86.6%. Further, in this step, silica gel column chromatography (hexane/ethyl acetate=3:1) was used for purification of the product.

$^1$H-NMR (CDCl$_3$): 1.48 (3H, dd, J=6.3, 23.4 Hz), 3.91 (3H, s), 4.07-4.16 (2H, m), 4.93-5.14 (1H, m), 7.08 (1H, dd, J=2.4, 8.8 Hz), 7.29 (1H, d, J=2.4 Hz), 7.86 (1H, d, J=8.8 Hz)

FAB+: 281

Step 9

Synthesis of 4-{[(2R)-2-fluoropropyl]oxy}-2-(trifluoromethyl)benzoic acid (Compound of the formula (7))

By the method described in Reference Example 33 of Patent Document 1, 4-{[(2R)-2-fluoropropyl]oxy}-2-(trifluoromethyl)benzoic acid was obtained in a yield of 97.1%.

$^1$H-NMR (CDCl$_3$): 1.39 (3H, dd, J=6.3, 23.4 Hz), 4.28-4.37 (2H, m), 4.95-5.15 (1H, m), 7.56-7.68 (2H, m), 7.87 (1H, d, J=8.3 Hz), 13.25 (1H, s)

FAB+: 267

Step 10

Synthesis of methyl 2-{(3-cyanopropyl)[(4-methylphenyl)sulfonyl]amino}-5-fluorobenzoate (compound of formula (21))

In the same manner to the method for producing the compound [3] described in Non-Patent Document 1, the reaction was carried out. Specifically, methyl 5-fluoro-2-{[(4-methylphenyl)sulfonyl]amino}benzoate (167 g), 2-butanone (500 mL), 4-chlorobutyronitrile (62.4 mL), potassium carbonate (142 g), and potassium iodide (25.7 g) were mixed, followed by stirred at 80° C. for 29 hours. The reaction mixture was subjected to a liquid separation operation by addition of water (500 mL). This organic layer was concentrated under reduced pressure, and then to the residue was added ethanol (1000 mL), followed by heating at 50° C. Further, water (500 mL) was added thereto, followed by cooling to 4° C. and stirring for 3 hours. The precipitated crystal was collected by filtration, washed with water, and then dried at 50° C. under reduced pressure to obtain methyl 2-{(3-cyanopropyl)[(4-methylphenyl)sulfonyl]amino}-5-fluorobenzoate (187 g) in a yield of 93.0%.

$^1$H-NMR (CDCl$_3$): 1.94 (2H, quintet, J=6.8 Hz), 2.43 (3H, s), 2.50-2.80 (2H, m), 3.52 (1H, br), 3.80-3.95 (4H, m), 6.82 (1H, dd, J=8.8 Hz, 4.8 Hz), 7.10-7.15 (1H, m), 7.26 (2H, d, J=7.6 Hz), 7.44 (2H, d, J=7.6 Hz), 7.56 (1H, dd, J=8.8 Hz, 3.2 Hz)

EI: 390

Step 11

Synthesis of 7-fluoro-1-[(4-methylphenyl)sulfonyl]-5-oxo-2,3,4,5-tetrahydro-1H-1-benzazepine-4-carbonitrile (compound of formula (20))

In the same manner to the method for producing the compound [4] described in Non-Patent Document 1, the reaction was carried out. Specifically, methyl 2-{(3-cyanopropyl)[(4-methylphenyl)sulfonyl]amino}-5-fluorobenzoate (153 g) and N,N-dimethylformamide (613 mL) were mixed, and to this solution was added potassium tert-butoxide (52.8 g) in divided portions under ice-cooling, followed by cooling and stirring at 10° C. to 20° C. for 5 hours. To this reaction mixture was added water (306 mL), followed by neutralization with concentrated hydrochloric acid (49.0 mL). To this reaction mixture was added water (612 mL) in divided portions, followed by stirring at 10° C. The precipitated crystal was collected by filtration, washed with water, and then dried at 50° C. under reduced pressure to obtain 7-fluoro-1-[(4-methylphenyl)sulfonyl]-5-oxo-2,3,4,5-tetrahydro-1H-1-benzazepine-4-carbonitrile (132.5 g) in a yield of 84.2%.

$^1$H-NMR (DMSO-d$_6$): 2.11 (2H, t, J=6.0 Hz), 2.40 (3H, s), 3.96 (2H, br), 7.30 (1H, dd, J=9.2 Hz, 2.8 Hz), 7.35-7.45 (4H, m), 7.51 (2H, d, J=8.4 Hz), 11.10 (1H, s)

EI: 358

Step 12

Synthesis of 7-fluoro-1-[(4-methylphenyl)sulfonyl]-1,2,3,4-tetrahydro-5H-1-benzazepin-5-one (compound of formula (12))

In the same manner to the method for producing the compound [5] described in Non-Patent Document 1, the reaction was carried out. Specifically, acetate (20 mL), concentrated hydrochloric acid (20 mL), and 7-fluoro-1-[(4-methylphenyl)sulfonyl]-5-oxo-2,3,4,5-tetrahydro-1H-1-benzazepine-4-carbonitrile (10.0 g) were mixed, followed by stirring at 65° C. for 3 hours, and then stirring at 85° C. to 90° C. for 18 hours. To this reaction mixture was added water (20 mL), and the mixture was neutralized by addition of a solution of sodium hydroxide (25.9 g) and water (100 mL) under ice-cooling and extracted by addition of ethyl acetate (60 mL), and further extracted by addition of ethyl acetate (40 mL) to the aqueous layer. The organic layers obtained by such two times extraction were combined, washed with a 10% aqueous sodium hydroxide solution (100 g), and then the solvent was evaporated therefrom under reduced pressure. To the obtained residue were added acetonitrile (40 mL), pyridine (6.75 mL), and p-toluenesulfonyl chloride (5.32 g), followed by stirring at room temperature for 18 hours. To this reaction mixture was added a solution of sodium hydroxide (1.17 g) and water (20 mL), followed by stirring for 24 hours, and then acetonitrile was evaporated therefrom under reduced pressure. This reaction mixture was extracted by addition of water (30 mL) and ethyl acetate (50 mL), and the aqueous layer was further extracted by addition of ethyl acetate (30 mL). The organic layers obtained by such two times extraction were combined and washed with a solution of concentrated hydrochloric acid (6.98 mL) and water (50 mL), and a solution of sodium chloride (2.5 g) and water (50 mL), and then the solvent was evaporated therefrom under reduced pressure. To the obtained residue were added ethanol (30 mL) and isopropanol (10 mL), followed by stirring at 10° C. The precipitated crystal was collected by filtration and dried at 50° C. under reduced pressure to obtain 7-fluoro-1-[(4-methylphenyl)sulfonyl]-1,2,3,4-tetrahydro-5H-1-benzazepin-5-one (8.42 g) in a yield of 90.5%.

$^1$H-NMR (DMSO-d$_6$): 1.85 (2H, quintet, J=6.0 Hz), 2.34-2.38 (2H, m), 2.41 (3H, s), 3.78 (2H, t, J=6.4 Hz), 7.29-7.33 (2H, m), 7.41 (2H, d, J=8.0 Hz), 7.49 (1H, dt, J=8.8 Hz, 2.8 Hz), 7.61 (2H, d, J=8.0 Hz)

Step 13

Synthesis of 4,4,7-trifluoro-1-[(4-methylphenyl)sulfonyl]-1,2,3,4-tetrahydro-5H-1-benzazepin-5-one (compound of formula (11))

In the same manner to the method for producing the compound [6] described in Non-Patent Document 1, the reaction was carried out. Specifically, acetonitrile (360 mL), 7-fluoro-1-[(4-methylphenyl)sulfonyl]-1,2,3,4-tetrahydro-5H-1-benzazepin-5-one (60 g), dimethyl sulfuric acid (25.6 mL), N,N'-difluoro-2,2'-bipyridium bis(tetrafluoroborate) (86.1 g), and concentrated sulfuric acid (9.6 mL) were mixed, following by stirring at 80° C. for 45 hours, and then the solvent was evaporated therefrom under reduced pressure. To the obtained residue were added ethyl acetate (480 mL), water (480 mL), and concentrated hydrochloric acid (30 mL), followed by stirring at room temperature and then carrying out a liquid separation operation, and the obtained aqueous layer was extracted by addition of ethyl acetate (240 mL). The obtained organic layers were combined and washed with water (300 mL), and water (300 mL) and sodium chloride (15 g) were then added thereto, followed by stirring. After filtration of insoluble materials, a liquid separation operation was carried out. The solvent of the organic layer was evaporated under reduced pressure, and to the obtained residue were added ethyl acetate (60 mL), toluene (360 mL), and activated carbon (12 g), followed by stirring at 60° C. Activated carbon was separated by filtration from the mixed solution and washed with toluene (120 mL). The filtrate and the washing liquid were combined, and the solvent was evaporated therefrom under reduced pressure. To the obtained residue was added toluene (90 mL), and n-heptane (240 mL) was further added thereto, followed by stirring at 20° C. The precipitated crystal was collected by filtration and dried at 50° C. under reduced pressure to obtain 4,4,7-trifluoro-1-[(4-methylphenyl)sulfonyl]-1,2,3,4-tetrahydro-5H-1-benzazepin-5-one (53.6 g) in a yield of 80.6%.

$^1$H-NMR (CDCl$_3$): 2.32-2.42 (2H, m), 2.43 (3H, s), 4.06-4.10 (2H, m), 7.19-7.26 (4H, m), 7.44 (2H, d, J=8.4 Hz), 7.50 (1H, dd, J=8.8 Hz, 4.8 Hz)

EI: 370

Step 14

Synthesis of (2Z)-{4,4,7-trifluoro-1-[(4-methylphenyl)sulfonyl]-1,2,3,4-tetrahydro-5H-1-benzazepin-5-ylidene}acetic acid dicyclohexylamine salt (compound of formula (9-S))

In the same manner to the method for producing the compound [7] described in Non-Patent Document 1, a (2Z)-{4,4,7-trifluoro-1-[(4-methylphenyl)sulfonyl]-1,2,3,4-tetrahydro-5H-1-benzazepin-5-ylidene}acetic acid dicyclohexylamine salt was obtained in a yield of 27.0%.

$^1$H-NMR (CDCl$_3$): 1.17-1.36 (8H, m), 1.50-1.70 (6H, m), 1.78-1.90 (4H, m), 2.06-2.17 (4H, m), 2.36 (3H, s), 2.40-2.55 (1H, m), 2.99-3.11 (2H, m), 3.90-4.03 (1H, m), 5.56 (1H, s), 6.93-7.01 (2H, m), 7.17 (2H, d, J=11 Hz), 7.37-7.42 (1H, m), 7.56 (2H, d, J=11 Hz)

FAB+: 412

Step 15

Synthesis of methyl (2Z)-(4,4,7-trifluoro-1,2,3,4-tetrahydro-5H-1-benzazepin-5-ylidene)acetate (compound of formula (8-M))

In the same manner to the method for producing compound [8] described in Non-Patent Document 1, methyl (2Z)-(4,4,7-trifluoro-1,2,3,4-tetrahydro-5H-1-benzazepin-5-ylidene)acetate was obtained.

$^1$H-NMR (CDCl$_3$): 2.47-2.63 (2H, m), 3.37 (2H, t, J=7.84 Hz), 3.80 (3H, s), 6.14 (1H, s), 6.56-6.63 (1H, m), 6.83-6.91 (1H, m), 6.93-6.98 (1H, m)

FAB+: 272

Step 16

Synthesis of methyl (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetate (compound of formula (6-M))

In the same manner as the method described in Reference Example 7 of Patent Document 1, methyl (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetate was obtained in an overall yield of the steps 15 and 16 of 86.5%.

$^1$H-NMR (CDCl$_3$): 1.43 (3H, dd, J=8.6, 31.2 Hz), 2.12-2.57 (2H, m), 3.01-3.30 (1H, m), 3.86 (3H, s), 3.98-4.19 (2H, m), 4.82-5.29 (2H, m), 6.16 (1H, s), 6.76-6.85 (2H, m), 7.03-7.12 (2H, m), 7.27-7.37 (2H, m)

FAB+: 520

Step 17

Synthesis of (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (compound of formula (5))

In the same manner as the method described in Reference Example 20 of Patent Document 1, (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid was obtained in a yield of 86.3%.

$^1$H-NMR (DMSO-d$_6$): 1.33 (3H, dd, J=8.8, 31.5 Hz), 2.34-2.40 (1H, m), 2.58-2.96 (1H, m), 3.01-3.29 (1H, m), 4.01-4.22 (2H, m), 4.75-5.06 (2H, m), 6.51 (1H, s), 6.70-6.76 (1H, m), 6.82-6.91 (1H, m), 7.01-7.08 (2H, m), 7.17-7.26 (2H, m)

FAB+: 506

Step 18

Synthesis of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (compound of formula (1))

In the same manner as the method described in Example 1 of Patent Document 1, α type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide was obtained in a yield of 54.7%.

$^1$H-NMR (DMSO-d$_6$): 1.32 (3H, dd, J=5.9, 29.8 Hz), 2.32-2.46 (1H, br), 2.61-2.84 (1H, br), 3.03-3.27 (2H, m), 3.44-3.51 (2H, m), 4.02-4.22 (2H, m), 4.74 (1H, t, J=5.3 Hz), 4.76-4.85 (1H, br), 4.87-5.06 (1H, m), 6.52 (1H, s), 6.70-6.78 (1H, m), 6.87 (1H, d, J=8.8 Hz), 7.00-7.08 (1H, m), 7.19 (2H, dd, J=2.9 Hz, 8.8 Hz), 7.24 (1H, d, J=2.9 Hz), 7.67 (1H, d, J=8.8 Hz), 8.47 (1H, t, J=5.4 Hz)

FAB+: 549

EXAMPLES

Next, the method for producing the compound of the formula (1) shown in the reaction scheme (II) of the present invention, and other embodiments of such the method of the present invention, shown in the reaction schemes (III), (IV), and (V) are specifically described in examples below. Further, the present invention is not limited to these examples and can be appropriately modified or altered according to a method apparent to a person skilled in the art within a range not departing from the purpose of the present invention. These modifications and alterations are also included in the present invention. Further, the respective compounds which are starting materials can be produced according to a method apparent to a person skilled in the art.

The steps 1 to 12 shown in the reaction scheme (II) were carried out as described below to synthesize the compound of the formula (1).

Example 1

Steps 1 to 3

Synthesis of 4-{[(2R)-2-fluoropropyl]oxy}-2-(trifluoromethyl)benzoic acid (compound of formula (7))

4-Fluoro-2-(trifluoromethyl)benzoic acid (a compound of the formula (7e) in which Lv is fluoro, that is, a compound of the formula (7e-F) shown in the reaction scheme (I) (i-2)) (50 g), ethyl acetate (250 mL), N,N-dimethylformamide (0.88 g), and thionyl chloride (42.9 g) were mixed, followed by stirring at 60° C. for 7 hours. The reaction solution was concentrated under reduced pressure, to the residue were added acetonitrile (150 mL) and pyridine (85.5 g), and 2-propanol (65.0 g) was added dropwise thereto, followed by stirring at room temperature for 4 hours. The reaction solution was concentrated under reduced pressure and the residue was subjected to a liquid separation operation by addition of toluene (200 mL) and water (200 mL). The obtained organic layers were combined and washed with a solution of concentrated hydrochloric acid (71.0 g) and water (200 mL), and then washed with a solution of sodium chloride (25 g) and water (200 mL), and then the organic layer was concentrated under reduced pressure. To the residue was added toluene (125 mL) and the solution was concentrated under reduced pressure to obtain an oily residue. To the residue were added tetrahydrofuran (350 mL), (2R)-2-fluoropropanol (30.9 g), and potassium tert-butoxide (35.9 g), followed by stirring at 0° C. for 5 hours. The reaction solution was subjected to a liquid separation operation by addition of ammonium chloride (12.85 g) and water (200 mL). The obtained organic layers were combined and washed with a solution of sodium chloride (50 g) and water (200 mL). The organic layer was concentrated under reduced pressure, and to the obtained residue were added a solution of sodium hydroxide (19.2 g) and water (120 mL), and methanol (360 mL), followed by stirring at 60° C. for 19 hours. To the reaction solution were added water (420 mL) and toluene (60 mL), and to the obtained aqueous layers was added concentrated hydrochloric acid (49.7 g) and crystallized. The resulting slurry was stirred at 20° C. The resulting crystal was filtered and washed with a 30% aqueous methanol solution (12 mL) to obtain crude crystal (76.8 g). To the crystal was added 1-propanol (192 mL) and water (144 mL), followed by heating at 55° C. to dissolve the crystal and then cooling. After confirming precipitation of the crystal, water (144 mL) was added thereto, followed by cooling to 0° C. The resulting crystal was collected by filtration, washed with an aqueous 1-propanol solution (36 mL of 1-propanol and 84 mL of water), and dried at 50° C. under reduced pressure to obtain 4-{[(2R)-2-fluoropropyl]oxy}-2-(trifluoromethyl)benzoic acid (50.28 g) as a white crystal in a yield of 78.6%.

$^1$H-NMR (CDCl$_3$): 1.48 (3H, dd, J=23.6 Hz, 6.4 Hz), 4.08-4.17 (2H, m), 4.95-5.11 (1H, m), 7.10 (1H, dd, J=8.8 Hz, 2.4 Hz), 7.34 (1H, d, J=2.4 Hz), 8.06 (1H, d, J=8.8 Hz)

Step 4

Synthesis of methyl 5-fluoro-2-{(4-methoxy-4-oxobutyl)[(4-methylphenylsulfonyl]amino}benzoate (compound of formula (14))

Under a nitrogen atmosphere, methyl 5-fluoro-2-{[(4-methylphenyl)sulfonyl]amino}benzoate (30.0 g) and N,N-dimethylformamide (105 mL) were added, followed by stirring at 20° C. A solution of 4-chlorobutyrate methyl (15.2 g) and N,N-dimethylformamide (15 mL), a solution of potassium carbonate (25.7 g) and N,N-dimethylformamide (15 mL), and a solution of potassium iodide (4.62 g) and N,N-dimethylformamide (15 mL) were added sequentially thereto, followed by warming to 80° C. and stirring for 8 hours. After confirming a disappearance of the starting material, a liquid separation operation was carried out by addition of toluene (210 mL) and water (240 mL). The obtained organic layer was washed with a solution of sodium chloride (7.5 g) and water (150 mL), and then the organic layer was concentrated under reduced pressure to adjust the amount to about 60 mL. To the residue were added toluene (150 mL) and the mixed solution was concentrated under reduced pressure. The obtained residue was used for the next reaction without purification.

Steps 5 and 6 (Continuous Process)

Synthesis of 7-fluoro-1-[(4-methylphenyl)sulfonyl]-1,2,3,4-tetrahydro-5H-1-benzazepin-5-one (compound of formula (12))

A mixture of the residue obtained in the step 4 and N,N-dimethylformamide (300 mL) was cooled to 0° C., and potassium tert-butoxide (13.0 g) was added thereto five times portionwise, followed by stirring at the same temperature for 3 hours. After confirming a disappearance of the starting material, 6 M hydrochloric acid (18.7 mL) and water (11.3 mL) were added thereto to give pH 4, thereby stopping the reaction.

The obtained mixture was heated to 120° C., followed by stirring for 7 hours. After confirming a disappearance of the starting material, the mixture was cooled to 70° C. After adding water (105 mL) thereto at 70° C., homogenization of the reaction system was confirmed, followed by cooling slowly to 50° C. and then precipitation of crystal was confirmed. Thereafter, the obtained mixture was heated to 60° C. and stirred for 30 minutes. Water (165 mL) was added thereto at 60° C., followed by stirring for 30 minutes, then cooling to 20° C., and stirring overnight. The resulting crystal was collected by filtration and the crystal was washed with water (150 mL). The obtained crystal was dried at 50° C. under reduced pressure to obtain 7-fluoro-1-[(4-methylphenyl)sulfonyl]-1,2,3,4-tetrahydro-5H-1-benzazepin-5-one (28.81 g) in an overall yield of the steps 4 to 6 of 93.1%.

$^1$H-NMR (CDCl$_3$): 1.88-1.94 (2H, m), 2.34-2.37 (2H, m), 2.41 (3H, s), 3.81-3.84 (2H, m), 7.18-7.28 (3H, m), 7.34-7.37 (1H, m), 7.42-7.45 (1H, m), 7.53-7.56 (2H, m)

ESI+: 333

Step 7

Synthesis of 4,4,7-trifluoro-1-[(4-methylphenyl)sulfonyl]-1,2,3,4-tetrahydro-5H-1-benzazepin-5-one (compound of formula (11))

By the same method as the step 13 of Reference Example, 4,4,7-trifluoro-1-[(4-methylphenyl)sulfonyl]-1,2,3,4-tetrahydro-5H-1-benzazepin-5-one was obtained in a yield of 80.6%.

Steps 8 and 9

Synthesis of methyl (2Z)-(4,4,7-trifluoro-1,2,3,4-tetrahydro-5H-1-benzazepin-5-ylidene)acetate (compound of formula (8) in which $R^1$ is methyl, that is, Formula (8-M) shown in reaction scheme (I) (ii))

Diphenylphosphonoacetic acid (5.93 g) was suspended in tetrahydrofuran (44 mL), followed by cooling to −66° C. to −59° C., and then sodium bis(trimethylsilyl)amide (1.9 M solution in tetrahydrofuran) (21.0 mL) was added dropwise thereto over 15 minutes. To this mixture was added dropwise a solution of 4,4,7-trifluoro-1-[(4-methylphenyl)sulfonyl]-1,2,3,4-tetrahydro-5H-1-benzazepin-5-one (5.00 g) in tetrahydrofuran (20 mL) which had been cooled in a dry ice/methanol bath, at −68° C. to −60° C. using a cannula, followed by washing with tetrahydrofuran (15 mL). After stirring at −60° C. or lower for 2.5 hours, the mixture was warmed to −20° C. to −15° C., followed by stirring for 18.5 hours. Water (30 mL) was added thereto, followed by concentration under reduced pressure until the amount of the reaction solution reached about 50 mL. To the obtained residue was added concentrated hydrochloric acid (5 mL), followed by extraction with 2-butanone (30 mL), and the obtained organic layer was washed with water (30 mL) and a 20% aqueous sodium chloride solution (sodium chloride 4 g, water (20 mL)) and then concentrated under reduced pressure until the amount reached about 10 mL. Toluene (25 mL) was added to the obtained residue, followed by concentration under reduced pressure until the amount reached about 10 mL, and this operation was repeated again. To the obtained residue were added toluene (25 mL) and sulfuric acid (7.5 mL), followed by stirring at 80° C. to 81° C. for 14.5 hours. The reaction solution was cooled to room temperature, and methanol (15 mL) was added thereto, followed by stirring at 60° C. to 62° C. for 4 hours. The reaction solution was cooled to room temperature, and water (25 mL) and 5 M aqueous sodium hydroxide solution (35 mL) were added thereto, followed by extraction with 2-butanone (15 mL), and the obtained aqueous layer was extracted with 2-butanone (15 mL) and toluene (15 mL). The obtained organic layers were combined and washed twice with a solution of sodium hydrogen carbonate (1.5 g) and water (30 mL), and once with water (30 mL). The obtained organic layer was concentrated under reduced pressure. To the residue was added toluene (15 mL), followed by heating to 50° C. to 60° C., and after confirming that crystal was dissolved, n-heptane (10 mL) was added dropwise thereto, and then precipitation of crystal was confirmed. After n-heptane (20 mL) was further added dropwise thereto, the reaction solution was cooled to 15° C., followed by stirring overnight. The resulting crystal was collected by filtration and washed with a mixed solvent of toluene (5 mL) and n-heptane (10 mL). The obtained crystal was dried under reduced pressure at 50° C. to obtain methyl (2Z)-(4,4,7-trifluoro-1,2,3,4-tetrahydro-5H-1-benzazepin-5-ylidene)acetate (2.90 g) in a yield of 79.2%.

$^1$H-NMR (CDCl$_3$, 400 MHz); 2.46-2.59 (2H, m), 3.31-3.38 (2H, m), 3.79 (3H, s), 3.92 (1H, br), 6.12 (1H, s), 6.55 (1H, dd, J=8.4 Hz, 4.4 Hz), 6.85 (1H, m), 6.93 (1H, dd, J=9.2 Hz, 3.2 Hz)

Step 10

Synthesis of methyl (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetate (compound of formula (6) in which $R^1$ is methyl, that is, formula (6-M) shown in reaction scheme (I) (iii))

To a mixed solution of 4-{[(2R)-2-fluoropropyl]oxy}-2-(trifluoromethyl)benzoic acid (12.5 g), toluene (100 mL), and N,N-dimethylformamide (171.6 mg) was added thionyl chloride (6.70 g) at room temperature, followed by stirring at 55° C. to 65° C. for 1 hour and 20 minutes. This reaction solution was concentrated under reduced pressure to obtain a residue A containing 4-{[(2R)-2-fluoropropyl]oxy}-2-(trifluoromethyl)benzoyl chloride. Separately, methyl (2Z)-(4,4,7-trifluoro-1,2,3,4-tetrahydro-5H-1-benzazepin-5-ylidene)acetate (12.1 g) was dissolved in acetonitrile (75 mL), and then pyridine (18.6 g) was added thereto at room temperature. To this solution were added dropwise a mixed solution of the residue A and acetonitrile (37.5 mL), followed by stirring at 50° C. to 57° C. for 14 hours. This reaction solution was concentrated under reduced pressure, and then ethyl acetate (125 mL) was added thereto, followed by further adding a solution of sodium hydroxide (2.83 g) and water (125 mL) in an ice bath, and then extracted. The obtained organic layer was washed sequentially with a solution of concentrated hydrochloric acid (22.5 g) and water (125 mL), and with a solution of sodium chloride (6.25 g) and water (125 mL), and then the solvent was evaporated therefrom under reduced pressure. Ethanol (112.5 mL) was added to the obtained residue and dissolved the residue by heating at 61° C., followed by adding dropwise water (75 mL) thereto and stirring at about 20° C. for 63.5 hours. The obtained crystal was collected by filtration, washed with a mixed solution of ethanol (15 mL) and water (10 mL), and then dried at 50° C. under reduced pressure to obtain methyl (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetate (20.5 g) in a yield of 88.5%.

$^1$H-NMR (DMSO-d$_6$): 1.33 (3H, dd, J=6.4, 23.6 Hz), 2.20-2.60 (2H, m), 3.10-3.55 (1H, m), 3.79 (3H, s), 4.02-4.25 (2H, m), 4.70-5.14 (2H, m), 6.61-7.55 (7H, m)

ESI+: 519

Step 11

Synthesis of (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (compound of formula (5))

Methyl (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetate (227.7 g), sodium hydroxide (26.3 g), water (910.8 mL), and ethanol (1366 mL) were mixed, followed by stirring at 25° C. for 12 hours, and then concentrated hydrochloric acid (58.5 mL) and crystal of (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (228 mg) produced in "(alternative method for step 11 of Example 1)" in Example 2 described later was added thereto, followed by stirring for 11 hours. Thereafter, to this mixture was added water (1139 mL), followed by stirring at 20° C. for 7 hours. The obtained crystal was collected by filtration, washed with water (455 mL), and then dried at 50° C. under reduced pressure to obtain (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (216.6 g) in a yield of 97.8%.

$^1$H-NMR (DMSO-$d_6$): 1.33 (3H, dd, J=24.0 Hz, 6.4 Hz), 2.20-2.60 (2H, m), 3.00-3.60 (1H, m), 4.03-4.34 (2H, m), 4.60-5.20 (2H, m), 6.52-7.55 (7H, m), 13.26 (1H, br)

ESI+: 506

Step 12

Synthesis of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (compound of formula (1))

(2Z)-{4,4,7-Trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (10.0 g), ethyl acetate (100 mL), and N,N-dimethylformamide (100 mg) were mixed, and to this mixture was added thionyl chloride (2.17 mL) at room temperature, followed by stirring at 65° C. for 2 hours and a half. This reaction solution was concentrated under reduced pressure to obtain a residue containing (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetyl chloride. The obtained residue was dissolved in acetonitrile (50 mL) and added dropwise to a solution of 2-aminoethanol (24.2 g) and acetonitrile (50 mL) at 5° C., followed by stirring for 1 hour. To this reaction mixture was added water (100 mL), and acetonitrile was evaporated therefrom under reduced pressure, followed by extraction by addition of ethyl acetate (100 mL). This organic layer was washed sequentially with a solution of concentrated hydrochloric acid (5 mL) and water (100 mL), and with a solution of sodium chloride (5 g) and water (100 mL), and then the solvent was evaporated therefrom under reduced pressure. To the obtained residue were added ethanol (30 mL), and then the solvent was evaporated again under reduced pressure. The obtained residue was dissolved in ethanol (80 mL), followed by filtration. To the obtained filtrate was added water (120 mL), followed by heating, and α type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (12 mg) was added thereto, followed by stirring at room temperature, then cooling, and stirring at 15° C. The resulting crystal was collected by filtration, washed with a 40% aqueous ethanol solution (20 mL), and then dried at 50° C. under reduced pressure to obtain α type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (9.26 g) in a yield of 85.3%.

$^1$H-NMR (DMSO-$d_6$): 1.33 (3H, dd, J=24.0 Hz, 6.8 Hz), 2.42 (1H, br), 2.67 (1H, br), 3.14 (1H, br), 3.25 (2H, dd, J=12.0 Hz, 6.0 Hz), 3.49 (2H, dd, J=12.0 Hz, 6.4 Hz), 4.01-4.21 (2H, m), 4.70 (1H, t, J=5.6 Hz), 4.78 (1H, br), 4.86-5.06 (1H, m), 6.51 (1H, s), 6.74 (1H, dd, J=8.8 Hz, 4.8 Hz), 6.88 (1H, d, J=8.8 Hz), 7.00-7.06 (2H, m), 7.20 (1H, dd, J=8.8 Hz, 3.2 Hz), 7.24 (1H, d, J=2.8 Hz), 8.39 (1H, t, J=5.6 Hz)

ESI+: 549

The results of X-ray powder diffraction measurement and DSC analysis of α type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide obtained in this step are shown in FIGS. 1 and 2.

Further, the measurement conditions for the X-ray powder diffraction and the DSC analysis are as follows.

The X-ray powder diffraction was measured using MXP18TAHF22 manufactured by Mac Science under the conditions of a tube of Cu, a tube current of 200 mA, a tube voltage of 40 kV, a sampling width of 0.020°, a scanning speed of 3°/min, a wavelength of 1.54056 angstroms, and a measurement diffraction angle (2θ) of 3° to 40°.

The DSC analysis was performed using TA Instruments TA 5000 under the conditions of a measurement temperature range of room temperature to 300° C., a heating speed of 10° C./min, nitrogen flow rate of 50 mL/min, and an aluminum sample pan.

Example 2

Alternative methods for several steps described in Example 1 will be described below as another embodiment of the present invention. These alternative methods can be appropriately carried out so as to produce the compound of the formula (1), instead of the method described in each step described in Example 1.

Alternative Method for Step 1 of Example 1

Synthesis of isopropyl 4-fluoro-2-(trifluoromethyl)benzoate (compound of formula (7c) in which Lv is fluoro)

4-Fluoro-2-(trifluoromethyl)benzoic acid (150 g), ethyl acetate (1200 mL), N,N-dimethylformamide (2.78 mL), and thionyl chloride (78.9 mL) were mixed, followed by stirring at 70° C. for 3 hours. The solvent of this reaction mixture was evaporated under reduced pressure to obtain a residue containing 4-fluoro-2-(trifluoromethyl)benzoyl chloride. To the obtained residue were added acetonitrile (450 mL) and pyridine (291 mL), and 2-propanol (450 mL) was added dropwise thereto, followed by stirring at room temperature for 30 minutes. This mixture was subjected to a liquid separation operation by addition of toluene (600 mL) and water (600 mL), followed by extraction by addition of toluene (600 mL) to the aqueous layer. The obtained organic layers were combined, washed with 3 M hydrochloric acid (1200 mL), and then further washed with a solution of sodium chloride (150 g) and water (900 mL), and the solvent was evaporated therefrom under reduced pressure to obtain isopropyl 4-fluoro-2-(trifluoromethyl)benzoate (165 g) in a yield of 91.5%.

$^1$H-NMR (CDCl$_3$): 1.37 (6H, d, J=6.0 Hz), 5.20-5.30 (1H, m), 7.28-7.31 (1H, m), 7.44 (1H, dd, J=2.4, 9.2 Hz), 7.82 (1H, dd, J=5.6, 8.8 Hz)

Alternative Method for Step 2 of Example 1

Synthesis of Compound of Formula (7a)

Isopropyl 4-fluoro-2-(trifluoromethyl)benzoate (3.00 g), 1,3-dimethyl-2-imidazolidinone (12 mL), toluene (3 mL), (2R)-2-fluoropropanol (1.40 g), and cesium carbonate (7.81 g) were mixed, followed by stirring at 25° C. to 50° C. for 27 hours. This reaction mixture was extracted by addition of toluene (15 mL) and water (36 mL). This organic layer was washed with water (30 mL) and the solvent was evaporated therefrom under reduced pressure to obtain an oily residue. The obtained residue was purified by silica gel chromatography (eluent: n-heptane/ethyl acetate=20/1→15/1→5/1) to obtain isopropyl (2R)-4-(2-fluoropropoxy)-2-(trifluoromethyl)benzoate (2.77 g, a yield of 77.8%, an Rf value=0.4 (n-heptane/ethyl acetate=5/1)), and (2R)-2-fluoropropyl 4-{[(2R)-2-fluoropropyl]oxy}-2-(trifluoromethyl)benzoate (0.59 g, a yield of 15.1%, an Rf value=0.26 (n-heptane/ethyl acetate=5/1)).

Isopropyl (2R)-4-(2-fluoropropoxy)-2-(trifluoromethyl)benzoate (compound of formula (7a) in which R is isopropyl)

$^1$H-NMR (DMSO-d$_6$): 1.30 (6H, d, J=6.0 Hz), 1.39 (3H, dd, J=5.6, 23.6 Hz), 4.18-4.37 (2H, m), 4.94-5.17 (2H, m), 7.33-7.37 (2H, m), 7.82 (1H, d, J=8.4 Hz)
ESI+: 309

(2R)-2-Fluoropropyl 4-{[(2R)-2-fluoropropyl]oxy}-2-(trifluoromethyl)benzoate (compound of formula (7a) in which R is (2R)-2-fluoropropyl)

$^1$H-NMR (DMSO-d$_6$): 1.32-1.43 (6H, m), 4.20-4.48 (4H, m), 4.91-5.13 (2H, m), 7.37-7.40 (2H, m), 7.91 (1H, d, J=8.4 Hz)
ESI+: 327

Alternative Method for Steps 2 and 3 of Example 1

Synthesis of Compound of Formula (7)

Isopropyl 4-fluoro-2-(trifluoromethyl)benzoate (6.00 g), 1,3-dimethyl-2-imidazolidinone (24 mL), toluene (6 mL), (2R)-2-fluoropropanol (3.37 g), and cesium carbonate (19.5 g) were mixed, followed by stirring at 55° C. for 5 hours, and then cesium carbonate (3.91 g) and water (0.3 mL) were added thereto, followed by stirring at 55° C. for 75 hours. This reaction mixture was extracted by addition of toluene (30 mL) and water (72 mL). This organic layer was washed with water (60 mL), and then the solvent was evaporated therefrom under reduced pressure. To the obtained residue were added sequentially a solution of sodium hydroxide (1.92 g) and water (12 mL), and methanol (36 mL), followed by stirring at 60° C. for 22 hours. To this mixture were added water (42 mL) and toluene (12 mL), and the aqueous layer was washed. To this aqueous layer was added concentrated hydrochloric acid (4.16 mL), followed by stirring at 20° C. The obtained crystal was collected by filtration, washed with a 30% aqueous methanol solution (12 mL), and then dried at 50° C. under reduced pressure to obtain 4-{[(2R)-2-fluoropropyl]oxy}-2-(trifluoromethyl)benzoic acid (5.37 g) in a yield of 84.2%.

$^1$H-NMR (CDCl$_3$): 1.49 (3H, dd, J=6.4 Hz, 23.2 Hz), 4.08-4.22 (2H, m), 4.96-5.14 (1H, m), 7.11 (1H, dd, J=2.8 Hz, 8.8 Hz), 7.35 (1H, d, J=2.8 Hz), 8.08 (1H, d, J=8.8 Hz)
ESI−: 264

Alternative Method for Step 11 of Example 1

Synthesis of Compound of Formula (5)

Methyl (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetate (16.0 g), sodium hydroxide (1.85 g), water (64 mL), and ethanol (96 mL) were mixed, followed by stirring at 20° C. for 19 hours, and then concentrated hydrochloric acid (4.1 mL) was added thereto, followed by stirring for 2 hours. Thereafter, to this mixture was added water (32 mL), followed by stirring at 25° C. for 16 hours. Water (48 mL) was further added thereto, followed by stirring at 20° C. for 23 hours. The resulting crystal was collected by filtration, washed with water (32 mL), and dried at 50° C. under reduced pressure to obtain (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (15.2 g) in a yield of 97.4%.

$^1$H-NMR (DMSO-d$_6$): 1.33 (3H, dd, J=24.0 Hz, 6.4 Hz), 2.20-2.70 (2H, m), 3.10-3.60 (1H, m), 4.03-4.21 (2H, m), 4.76 (1H, br), 4.86-5.06 (1H, m), 6.54-7.55 (7H, m), 13.31 (1H, br)
ESI+: 506

Alternative Method 1 for Step 12 of Example 1

Synthesis of Compound of Formula (1)

(2Z)-{4,4,7-Trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (5.0 g), ethyl acetate (50 mL), and N,N-dimethylformamide (50 mg) were mixed, and to this mixture was added thionyl chloride (1.77 g) at room temperature, followed by stirring at 64° C. for 4 hours and a half. The solvent of the reaction mixture was evaporated under reduced pressure to obtain a residue containing (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetyl chloride. The residue was dissolved in acetonitrile (25 mL), and the solution was added dropwise to a mixed solution of 2-aminoethanol (12.1 g) and acetonitrile (25 mL) at 5° C., followed by stirring for 1 hour. To this reaction mixture was added water (50 mL), and acetonitrile was evaporated therefrom under reduced pressure, followed by extraction by addition of ethyl acetate (50 mL). This organic layer was washed sequentially with a solution of concentrated hydrochloric acid (2.5 g) and water (50 mL), and a solution of sodium chloride (2.5 g) and water (50 mL), and then the solvent was evaporated therefrom under reduced pressure. A half the residue thus obtained was taken out and isopropyl acetate (15 mL) was added thereto, followed by heating and dissolving at 78° C., and adding n-heptane (15 mL) dropwise thereto at the same temperature. After cooling to 10° C., the resulting crystal was stirred at 10° C. overnight. The resulting crystal was collected by filtration and dried at 50° C. under reduced pressure to obtain α type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (2.31 g, a yield of 85.1%, as converted in terms of case of using an overall amount).

Alternative Method 2 for Step 12 of Example 1

Synthesis of Compound of Formula (1)

(2Z)-{4,4,7-Trifluoro-1-[4-{[(2R)-2-fluoropropyl]oxy}-2-(trifluoromethyl)benzoyl]-1,2,3,4-tetrahydro-5H-1-benzazepin-5-ylidene}acetic acid (1.0 g), ethyl acetate (10 mL), and N,N-dimethylformamide (catalytic amount) were mixed, and to this mixed solution was added thionyl chloride (217 μL), followed by stirring at 65° C. for 1 hour. Thereafter, the solvent of this reaction mixture was evaporated under reduced pressure to obtain a residue containing (2Z)-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetyl chloride. The residue was dissolved in acetonitrile (10 mL) and the solution was added dropwise to a mixed solution of 2-aminoethanol (2.42 g) and acetonitrile (10 mL) under ice-cooling, followed by stirring for 30 minutes. To this reaction mixture was added water (20 mL), and acetonitrile was evaporated therefrom under reduced pressure, followed by extraction by addition of ethyl acetate (20 mL). This organic layer was washed sequentially with 0.6 M hydrochloric acid (20 mL), and water (20 mL), and then the solvent was evaporated therefrom under reduced pressure. To the obtained residue was added 2-propanol, and then the solvent was evaporated therefrom under reduced pressure. To the obtained residue was added 2-propanol (2 mL), followed by stirring, and n-heptane (8 mL) was added thereto, followed by stirring for 4 hours. The resulting crystal was collected by filtration, washed with n-heptane (2 mL), and then dried at 50° C. under reduced pressure to obtain β type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide (896 mg) in a yield of 83.0%.

$^1$H-NMR (DMSO-$d_6$): 1.33 (3H, dd, J=6.0, 23.6 Hz), 2.41 (1H, br), 2.67 (1H, br), 3.13 (1H, br), 3.23 (2H, dd, J=6.0, 12.0 Hz), 3.48 (2H, dd, J=6.0, 11.6 Hz), 4.01-4.21 (2H, m), 4.69 (1H, t, J=5.2 Hz), 4.78 (1H, br), 4.86-5.05 (1H, m), 6.50 (1H, s), 6.74 (1H, dd, J=5.2, 8.8 Hz), 6.87 (1H, d, J=8.8 Hz), 7.00-7.06 (2H, m), 7.19 (1H, dd, J=2.8, 8.8 Hz), 7.23 (1H, d, J=2.4 Hz), 8.38 (1H, t, J=6.0 Hz)

FAB+: 549

The results of X-ray powder diffraction measurement and DSC analysis of the β type crystal of (2Z)—N-(2-hydroxyethyl)-2-{4,4,7-trifluoro-1-[4-{[(2R)-2-fluoropropyl]oxy}-2-(trifluoromethyl)benzoyl]-1,2,3,4-tetrahydro-5H-1-benzazepin-5-ylidene}acetamide obtained in this step are shown in FIGS. 3 and 4.

Further, the measurement conditions for each analysis are the same as those described in the step 12 of Example 1.

Example 3

Each step shown in the reaction scheme (III) was carried out as follows to obtain the compound of the formula (7).

Step A

Synthesis of 4-{[(2R)-2-Fluoropropyl]oxy}-2-(trifluoromethyl)benzoic Acid (compound of formula (7))

Under a nitrogen atmosphere, (2R)-2-fluoropropanol (112.6 g) and 4-fluoro-2-(trifluoromethyl)benzoic acid (the compound of the formula (7e-F)) (166.7 g) was dissolved in 1,3-dimethyl-2-imidazolidinone (1000 mL), and then 60% sodium hydride (89.7 g) was added thereto at 20° C. to 30° C., followed by stirring at 30° C. for 2 days. This reaction mixture was cooled, water (3000 mL) was added thereto, ethyl acetate (834 mL) and concentrated hydrochloric acid (200 mL) were added sequentially thereto, and after confirming that the aqueous layer was acidic, the mixture was extracted. An operation of extraction by addition of ethyl acetate (500 mL) to the aqueous layer was carried out twice. The organic layers obtained by these three extraction operations were combined, and the solvent was evaporated therefrom under reduced pressure. To the obtained residue was added n-heptane (500 mL), followed by washing with a solution of sodium hydroxide (48.1 g) and water (833 mL), and the organic layer was further washed with water (167 mL). The aqueous layers caused by washing twice were combined, and ethyl acetate (833 mL) and concentrated hydrochloric acid (107 mL) were added sequentially thereto, followed by stirring and extraction. The solvent of this organic layer was evaporated under reduced pressure. To the obtained residue was added methanol (583 mL), and then water (1084 mL) was added thereto at 25° C. to 30° C., followed by stirring at 20° C. for 30 minutes. The resulting crystal was collected by filtration, washed sequentially with a mixed solution of methanol (50 mL) and water (116.7 mL), and water (166.7 mL), and dried at 50° C. under reduced pressure to obtain a crude crystal (155 g). The crude crystal was dissolved in methanol (620 mL), and then water (930 mL) was added thereto at 17° C. to 28° C., followed by stirring at 20° C. for 30 minutes. The resulting crystal was collected by filtration, washed sequentially with a mixed solution of methanol (46.5 mL) and water (108.5 mL), and water (155 mL), and dried at 50° C. under reduced pressure to obtain a crude crystal (134 g). To the crude crystal was added n-propanol (423 mL), followed by heating and dissolving at 66° C., and water (643 mL) was slowly added thereto, followed by stirring at 15° C. overnight. The resulting crystal was collected by filtration, washed with a mixed solution of n-propanol (80 mL) and water (188 mL), and dried at 50° C. under reduced pressure to obtain 4-{[(2R)-2-fluoropropyl]oxy}-2-(trifluoromethyl)benzoic acid (116 g) in a yield of 54.4%.

$^1$H-NMR (CDCl$_3$): 1.49 (3H, dd, J=23.2 Hz, 6.0 Hz), 4.08-4.22 (2H, m), 4.94-5.15 (1H, m), 7.11 (1H, dd, J=8.8 Hz, 2.4 Hz), 7.35 (1H, d, J=2.4 Hz), 8.06 (1H, d, J=8.8 Hz)

ESI−: 265

This alternative step is excellent in efficiency from the viewpoint that the compound of the formula (7) can be produced in one step from the starting compound of the formula (7e-F).

Example 4

Each step shown in the reaction scheme (IV) was carried out as follows to obtain the compound of the formula (7).

Step B

Synthesis of methyl 4-[(2S)-oxiran-2-ylmethoxy]-2-(2-trifluoromethyl)benzoate (compound of formula (7g) in which $R^2$ is methyl)

Methyl 4-hydroxy-2-(trifluoromethyl)benzoate (1.4 g), N,N-dimethylformamide (10 mL), potassium carbonate (1.14 g), and cesium fluoride (195 mg) were mixed, followed by stirring at room temperature for 40 minutes. To this reaction solution was added (S)-glycidyl 3-nitrobenzenesulfonate (1.65 g), followed by stirring at room temperature for 15 hours and 20 minutes. To the reaction solution was added ethyl acetate (15 mL), the insoluble materials were filtered, and the insoluble materials were further washed with ethyl acetate (10 mL). To the combined ethyl acetate solution was added water, and the organic layer was washed with water, a saturated aqueous sodium chloride solution, and then dried over anhydrous sodium sulfate. The solvent was evaporated therefrom under reduced pressure to obtain methyl 4-[(2S)-oxiran-2-ylmethoxy]-2-(2-trifluoromethyl)benzoate (1.825 g).

¹H-NMR (CDCl₃): 2.77 (1H, dd, J=4.4 Hz, 2.8 Hz), 2.94 (1H, t, J=2.8 Hz), 3.36-3.38 (1H, m), 3.91 (3H, s), 4.00 (1H, dd, J=10.8 Hz, 6.0 Hz), 4.36 (1H, dd, J=10.8 Hz, 2.4 Hz), 7.09 (1H, dd, 8.8 Hz, 2.8 Hz), 7.29 (1H, d, J 2.8 Hz), 7.84 (1H, d, J=8.8 Hz)

Step C

Synthesis of methyl 4-{[(2S)-2-hydroxypropyl]oxy}-2-(2-trifluoromethyl)benzoate (compound of formula (7f) in which R² is methyl, that is, formula (7f-M) shown in reaction scheme (I) (i-2))

To a suspension of 10% palladium carbon (55 mg) in ethanol (20 mL) were added methyl 4-[(2S)-oxiran-2-ylmethoxy]-2-(2-trifluoromethyl)benzoate (750 mg) and ammonium formate (516 mg), followed by stirring at room temperature for 2 hours and 15 minutes. The reaction solution was filtered and the filtrate was concentrated under reduced pressure. To the obtained residue were added ethyl acetate and water, and the organic layer was washed with a saturated aqueous sodium chloride solution and then dried over anhydrous sodium sulfate. The solvent was evaporated therefrom under reduced pressure to obtain methyl 4-{[(2S)-2-hydroxypropyl]oxy}-2-(2-trifluoromethyl)benzoate (727 mg) in a yield of 96.0%.

¹H-NMR (CDCl₃): 1.32 (3H, d, J=6.4 Hz), 3.88-3.93 (4H, m), 3.98 (1H, dd, J=9.6 Hz, 2.4 Hz), 4.19-4.27 (1H, m), 7.07 (1H, dd, J=8.8 Hz, 2.4 Hz), 7.28 (1H, d, J=2.4 Hz), 7.85 (1H, d, J=8.8 Hz)

FAB+: 279

Step D

Synthesis of 4-{[(2R)-2-fluoropropyl]oxy}-2-(trifluoromethyl)benzoic acid (compound of formula (7))

To a solution of methyl 4-{[(2S)-2-hydroxypropyl]oxy}-2-(2-trifluoromethyl)benzoate (645 mg) in dichloromethane (15 mL) was added (diethylamino)sulfur trifluoride (0.62 mL) at −78° C., followed by stirring at room temperature for 21 hour 15 minutes. To the reaction solution were added a cooled saturated aqueous sodium hydrogen carbonate solution and chloroform, and the organic layer was washed sequentially with 1 M hydrochloric acid, water, and a saturated aqueous sodium chloride solution, and then dried over anhydrous sodium sulfate to evaporate the solvent. To a solution of the obtained residue in methanol (10 mL) was added a 5 M aqueous sodium hydroxide solution (1 mL), followed by stirring at 70° C. for 5 hours. The reaction solution was concentrated under reduced pressure, to the obtained residue were added water, chloroform, and a 1 M aqueous sodium hydroxide solution, and the obtained aqueous layer was adjusted to pH 1 using 1 M hydrochloric acid, followed by extraction with chloroform. The organic layer was washed sequentially with water and a saturated aqueous sodium chloride solution, and then dried over anhydrous sodium sulfate. The solvent was evaporated, and to the obtained residue was added an ethanol:water (40:60) mixed solvent (5 mL), followed by stirring at room temperature for 3 hours and 30 minutes. The resulting solid was filtered and dried to obtain 4-{[(2R)-2-fluoropropyl]oxy}-2-trifluoromethyl)benzoic acid (465 mg) in a yield of 75.4%.

¹H-NMR (CDCl₃): 1.49 (3H, dd, J=23.6 Hz, 6.4 Hz), 4.11-4.19 (2H, m), 4.95-5.14 (1H, m), 7.11 (1H, dd, J=8.4 Hz, 2.4 Hz), 7.35 (1H, d, J=2.4 Hz), 8.07 (1H, d, J=8.4 Hz)

Example 5

Each step shown in the reaction scheme (V) was carried out as follows to obtain the compound of the formula (8) in which R¹ is methyl, that is, the compound of the formula (8-M) shown in the reaction scheme (I) (ii).

Step E

Synthesis of (2Z)-{4,4,7-trifluoro-1-[(4-methylphenyl)sulfonyl]-1,2,3,4-tetrahydro-5H-1-benzazepin-5-ylidene}acetic acid dicyclohexylamine salt (compound of formula (9-S))

To a suspension of 60% sodium hydride (1.08 g) in tetrahydrofuran (400 mL) was added 4,4,7-trifluoro-1-[(4-methylphenyl)sulfonyl]-1,2,3,4-tetrahydro-5H-1-benzazepin-5-one (50.0 g), followed by stirring for 40 minutes under water-cooling, and then cooling to −70° C. To the reaction solution was added dropwise a solution of diethylphosphonoacetic acid (29.2 g) in tetrahydrofuran (100 mL), followed by stirring at the temperature for 10 minutes. Sodium tert-butoxide (28.6 g) was added dropwise thereto in four divided portions, followed by stirring for 21 hours while warming to −20° C. To the reaction solution were added water and concentrated hydrochloric acid, followed by extraction with ethyl acetate. The organic layer was washed with water and then concentrated under reduced pressure. To the obtained residue was added methanol and dicyclohexylamine, followed by stirring at room temperature for 22 hours. The precipitated solid was collected by filtration, and the solid was washed with methanol/ethyl acetate and then dried under reduced pressure to obtain (2Z)-{4,4,7-trifluoro-1-[(4-methylphenyl)sulfonyl]-1,2,3,4-tetrahydro-5H-1-benzazepin-5-ylidene}acetic acid dicyclohexylamine salt (56.2 g) as a pale brown solid in a yield of 70.1%.

Step F

Synthesis of methyl (2Z)-(4,4,7-trifluoro-1,2,3,4-tetrahydro-5H-1-benzazepin-5-ylidene)acetate (compound of formula (8-M))

Methyl (2Z)-(4,4,7-trifluoro-1,2,3,4-tetrahydro-5H-1-benzazepin-5-ylidene)acetate was obtained from the compound of the formula (9-S) in the same manner as in the method for producing the compound of the formula [8] described in Non-Patent Document 1.

The effects of the present invention are shown below.

The yields of the production methods of the present invention of Example 1 are as shown in Table 1 below. Table 1 shows the individual yields of the steps 1 to 3 (continuous process), the steps 4 to 6 (continuous process), the step 7, the steps 8 to 9 (continuous process), the step 10, and the steps 11 and 12, and the overall yields of the steps 4 to 12 described in the Example.

TABLE 1

| Step | Yield (%) |
|---|---|
| Steps 1 to 3 | 78.6 |
| Steps 4 to 6 | 93.1 |
| Step 7 | 80.6 |
| Steps 8 to 9 | 79.2 |
| Step 10 | 88.5 |

TABLE 1-continued

| Step | Yield (%) |
| --- | --- |
| Step 11 | 97.8 |
| Step 12 | 85.3 |
| Overall yield of steps 4 to 12 | 43.9 |

On the other hand, the yield of a known method for producing the compound of the formula (1) described in the Reference Example, is as shown in Table 2 below.

TABLE 2

| Step | Yield (%) |
| --- | --- |
| Step 1 | 48.4 |
| Step 2 | 94.6 |
| Step 3 | 93.8 |
| Overall yield of steps 4 and 5 (successive steps) and step 6 | 65.6 |
| Step 7 | 82.6 |
| Step 8 | 86.6 |
| Step 9 | 97.1 |
| Overall yield of steps 3 to 9 | 42.7 |
| Step 10 | 93.0 |
| Step 11 | 84.2 |
| Step 12 | 90.5 |
| Step 13 | 80.6 |
| Step 14 | 27.0 |
| Overall yield of steps 15 and 16 | 86.5 |
| Step 17 | 86.3 |
| Step 18 | 54.7 |
| Overall yield of steps 10 to 18 | 6.30 |

From Tables 1 and 2, a comparison of the features of each corresponding step in the Example and the Reference Example and the yields thereof are shown below.

(Step for Producing Compound of Formula (7) from Compound of Formula (7e-F)/(7e))

Overall yield of the steps 1 to 3 of Example 1: 78.6%

Overall yield of the steps 3 to 9 of Reference Example: 42.7%

The method of producing the compound of the formula (7) shown in the steps 1 to 9 of Reference Example, required nine steps in total, and the method is not necessarily satisfactory in terms of efficiency since it includes a step of deprotection of a benzyl group, and steps of protection and deprotection of an acetyl group.

On the other hand, in the method of producing the compound of the formula (7) shown in the steps 1 to 3 of Example 1, the compound of the formula (7) can be produced in a high yield from the compound of the formula (7e) with three steps by using appropriate starting materials and reagents, and further, use of DAST which causes concern for safety can be avoided.

Moreover, the method for producing the compound of the formula (7) shown in the steps B to D of the reaction scheme (IV) in Example 4 is an advantageous method in efficiency, since the purification steps by silica gel column chromatography employed in the steps 1 to 2 and the steps 7 to 8 in Reference Example are not required, although DAST is used, and since the compound of the formula (7) can be produced with three steps, the steps B to D, from the compound of the formula (7i), as compared with Reference Example 1 in which six steps are required to obtain the compound of the formula (7) from the compound of the formula (7i-M), as shown in the reaction scheme (I) (i) and (ii).

Furthermore, in the esterification reaction shown in the step 1 of Example 1, introduction of an isopropyl ester could suppress generation of side products during the aromatic nucleophilic substitution reaction in the step 2, compared to other lower alkyl esters such as methyl ester and ethyl ester.

(Step of Producing Compound of Formula (12) from Compound of Formula (16))

Steps 4 to 6 of Example 1: 93.1%

Steps 10 to 12 of Reference Example: 70.9% (calculated by multiplying the yields of three steps)

In the step 12 of Reference Example, since a partial elimination of p-toluenesulfonyl group is observed during the reaction, it is necessary to introduce again the p-toluenesulfonyl group as a protecting group for the crude product of compound of the formula (12), and therefore, the step is not necessarily satisfactory in terms of cost and efficiency.

On the other hand, in the step 6 of the Example, the compound of the formula (12) could be produced without any elimination of the p-toluenesulfonyl group by using the compound of the formula (13) as an intermediate for synthesis. Further, the step is advantageous in terms of efficiency from the viewpoint that the compound of the formula (12) can be produced without isolating the intermediate compounds of the formulae (14) and (13).

(Step of Producing Compounds of Formula (6-M)/(6) from Compound of Formula (11))

Steps 8 to 10 of Example 1: 70.1%

(Calculated by Multiplying the Overall Yield of 8 to 9 Steps with the Yield of the Step 10)

Steps 14 to 16 of Reference Example: 24.8%

(Calculated by Multiplying the Yield of the Step 14 with the Overall Yield of the Steps 15 to 16)

In the steps 14 and 15 of Reference Example 1, in the reaction diethylphosphonoacetic acid is used. However, in such case, in order to produce a compound having double bonds in the Z forms selectively, it is necessary to produce dicyclohexylamine salt of the formula (9-S) at first in ethyl acetate, and then produce the compound of the formula (8-M).

On the other hand, in the step 8 of Example 1, by using diphenylphosphonoacetic acid as a reagent, the compound of the formula (8) having a ratio of E/Z of double bonds of 1/24, a high selectivity to the Z forms, could be produced in a high yield without any isolation of a dicyclohexylamine salt.

In addition, the method for producing the compound of the formula (9-S) shown in the steps E-(1) and E-(2) in the reaction scheme (V) in Example 5 is suitable from the viewpoint that the compound of the formula (9-S) can be produced in a high yield, as compared with the step 14 of Reference Example 1

(Step of Producing Compound of Formula (9-S) from Compound of Formula (11))

Step E of Example 5: 70.1%

Step 14 of Reference Example: 27.0%

In the step 14 of Reference Example, the compound of the formula (9-S) was produced by a treatment with dicyclohexylamine in ethyl acetate, and the yield thereof was 27.0%.

On the other hand, in the step E of Example 5, the compound of the formula (9-S) could be produced by a treatment with dicyclohexylamine in methanol in a yield of 70.1%.

(Step of Producing Compound of Formula (1) from Compound of Formula (5))

Step 12 of Example 1: 85.3%

Step 18 of Reference Example: 54.7%

It is necessary to use 1-ethyl-3-(3-dimethylaminopropyl) carbodiimide hydrochloride (EDC) exhibiting mutagenicity in an amidation reaction in the step 18 of Reference Example.

On the other hand, in the step 12 of Example 1, by affording an acid chloride using thionyl chloride and then reacting it with 2-aminoethanol, it is possible to increase the yield and avoid the use of EDC.

As described above, the production method of the present invention can maintain a high overall yield in all the steps without including steps with a yield of 50% or less in each step, as compared with known production methods, and thus, is advantageous in cost. In addition, the production method of the present invention is a production method which is an excellent, in particular suitable for industrial production of compound of the formula (1) as a medicament, without requiring purification by column chromatography and not requiring DAST or EDC having a concern about safety or toxicity risk.

INDUSTRIAL APPLICABILITY

The present invention provides a method for producing the compound of the formula (1) which has a high yield and a low cost and can be suitably used for industrial production of a medicament, as well as synthetic intermediates which are useful for use in the production method.

The invention claimed is:

1. A method for producing a compound of formula (1) shown in a reaction scheme below, comprising:
   a step of reacting a compound of formula (5) with thionyl chloride (4) to produce a compound of formula (3); and
   a step of amidating the compound of formula (3) by reacting with 2-aminoethanol (2):

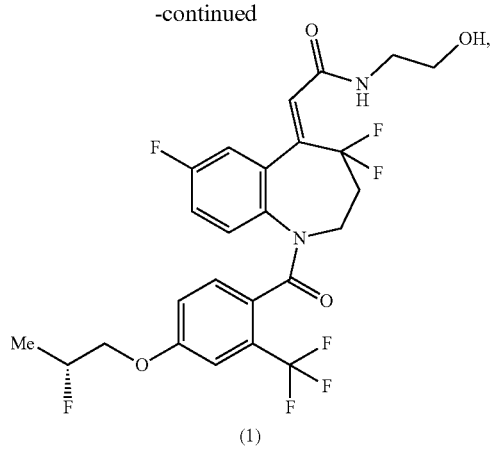

wherein Me represents methyl.

2. A method for producing a compound of formula (1) shown in a reaction scheme below, comprising:
   a step of producing a compound of formula (6) from a compound of formula (8) and a compound of formula (7);
   a step of producing a compound of formula (5) from the compound of formula (6);
   a step of producing a compound of formula (3) by reacting the compound of formula (5) with thionyl chloride (4); and
   a step of amidating the compound of formula (3) by reacting with 2-aminoethanol (2):

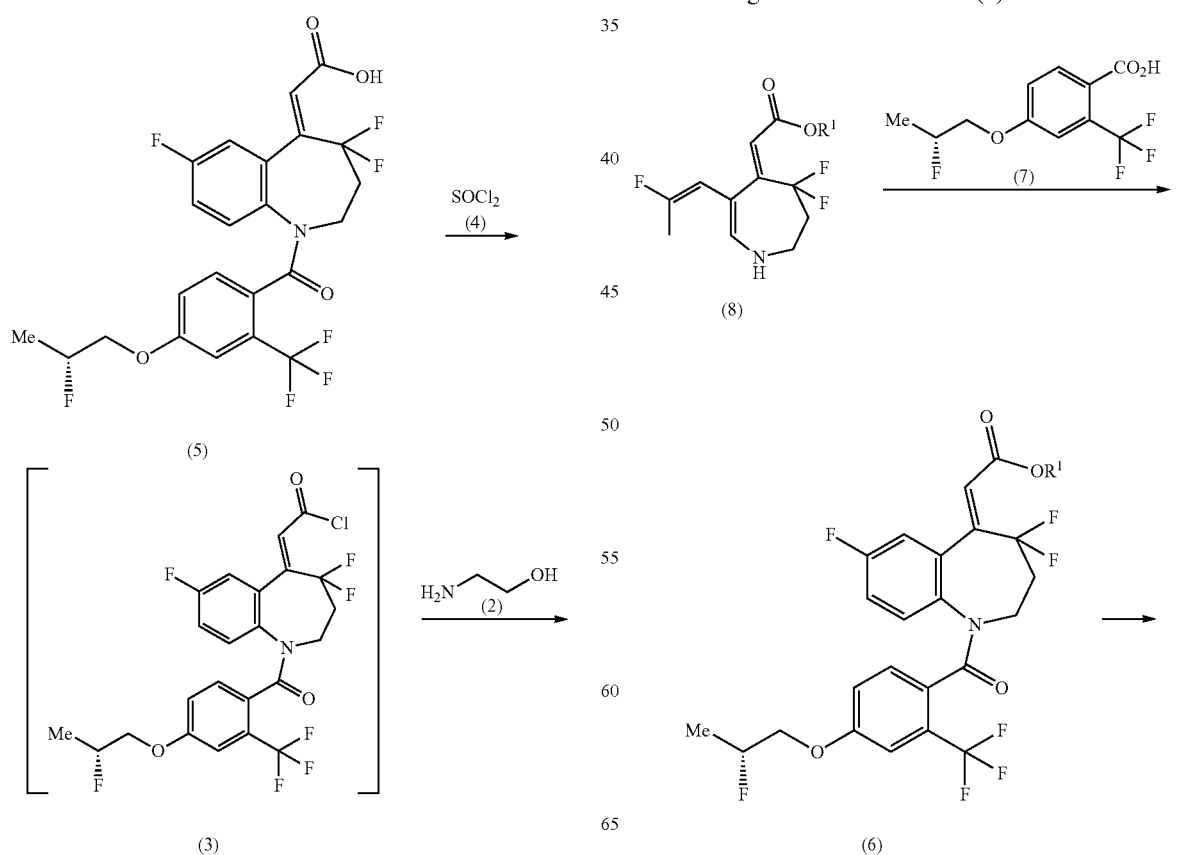

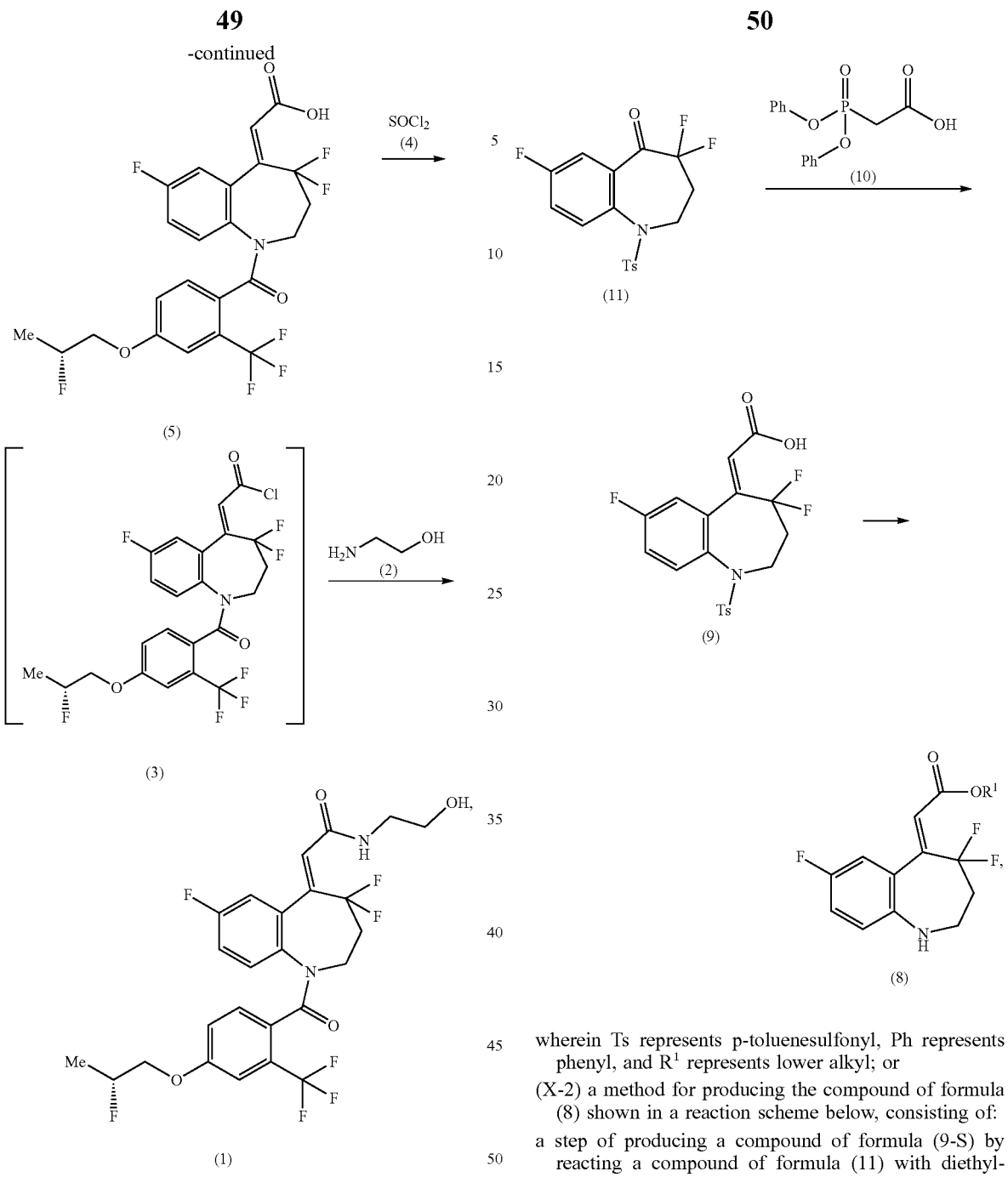

wherein Me represents methyl and R¹ represents lower alkyl.

3. The method for producing a compound of formula (1) according to claim 2, using the compound of formula (8) produced by:

(X-1) a method for producing the compound of formula (8) shown in a reaction scheme below, consisting of:

a step of producing a compound of formula (9) from a compound of formula (11) and diphenylphosphonoacetic acid (10), and a step of producing the compound of formula (8) from the compound of formula (9):

wherein Ts represents p-toluenesulfonyl, Ph represents phenyl, and R¹ represents lower alkyl; or (X-2) a method for producing the compound of formula (8) shown in a reaction scheme below, consisting of:

a step of producing a compound of formula (9-S) by reacting a compound of formula (11) with diethylphosphonoacetic acid (18), and treating the obtained crude product with dicyclohexylamine (17) in methanol, and a step of producing the compound of formula (8) from the compound of formula (9-S):

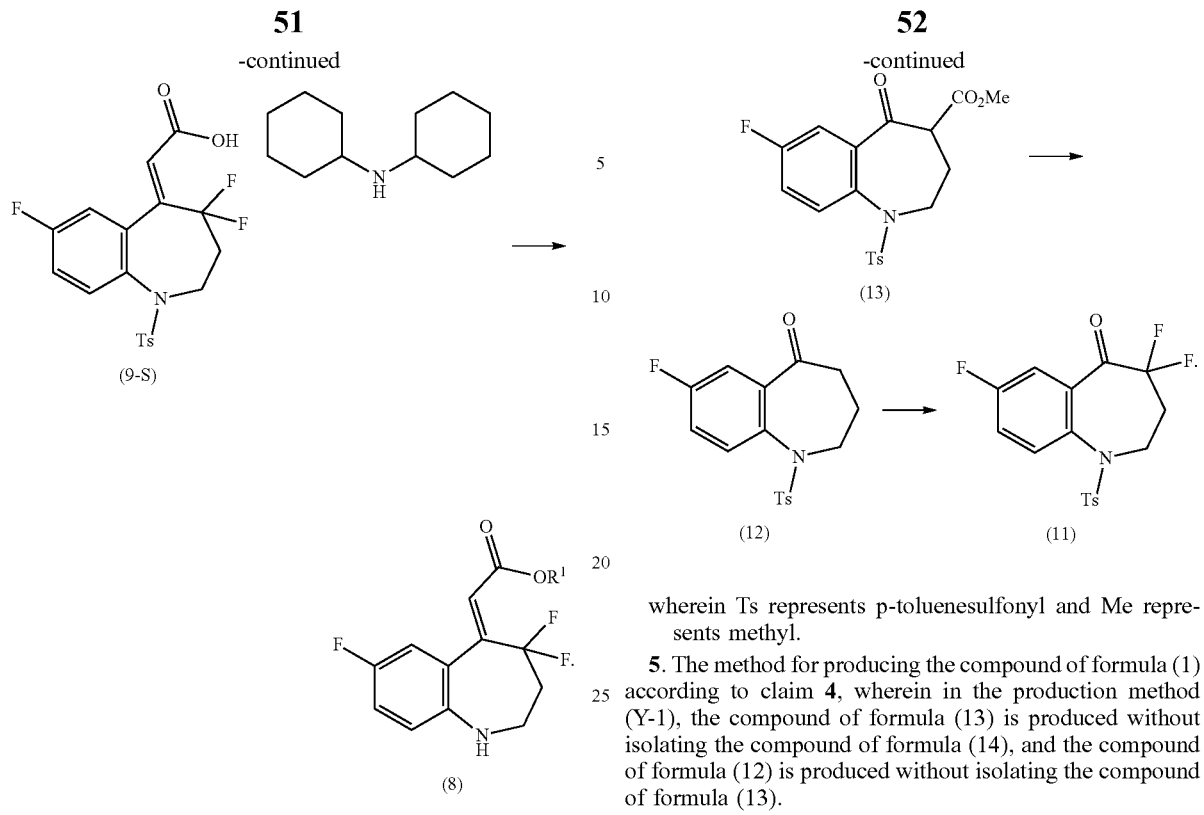

wherein Ts represents p-toluenesulfonyl, Et represents ethyl, and $R^1$ represents lower alkyl.

4. The method for producing the compound of formula (1) according to claim 3, using the compound of formula (11) produced by:

(Y-1) a method for producing the compound of formula (11) shown in a reaction scheme below, consisting of:
a step of producing a compound of formula (14) from a compound of formula (16) and methyl 4-chlorobutyrate (15),
a step of producing a compound of formula (13) from the compound of formula (14),
a step of producing a compound of formula (12) from the compound of formula (13), and
a step of producing the compound of formula (11) from the compound of formula (12):

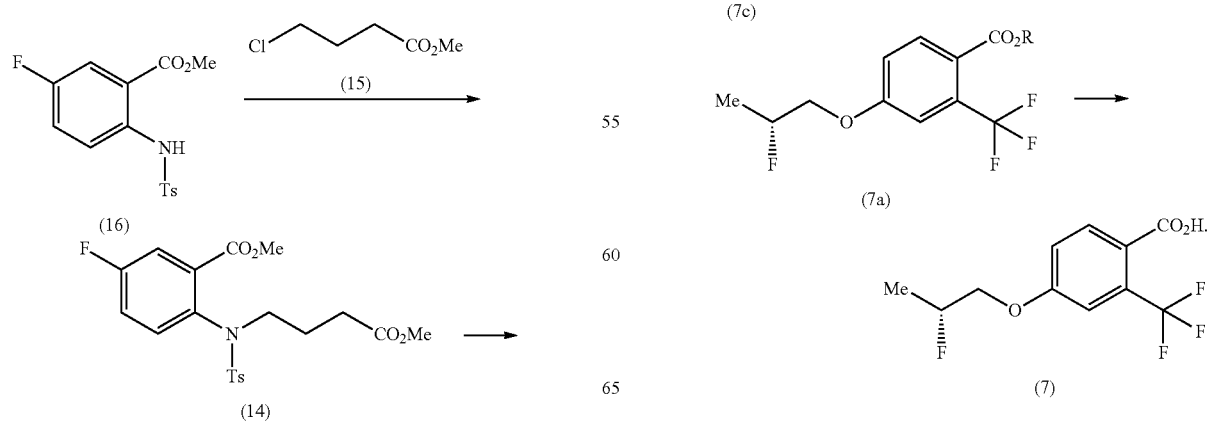

wherein Ts represents p-toluenesulfonyl and Me represents methyl.

5. The method for producing the compound of formula (1) according to claim 4, wherein in the production method (Y-1), the compound of formula (13) is produced without isolating the compound of formula (14), and the compound of formula (12) is produced without isolating the compound of formula (13).

6. The method for producing the compound of formula (1) according to any one of claims 2 to 5, using the compound of formula (7) produced by any one of:

(Z-1) a method for producing the compound of formula (7) shown in a reaction scheme below, consisting of:
a step of producing a compound of formula (7a) from a compound of formula (7c) and (2R)-2-fluoropropanol (7b), and
a step of producing the compound of formula (7) from the compound of formula (7a):

wherein Lv represents leaving group, Me represents methyl, iPr represents isopropyl, and R represents isopropyl or (2R)-2-fluoropropyl;

(Z-2) a method for producing the compound of formula (7) shown in a reaction scheme below, which is a step of producing the compound of formula (7) from the compound of formula (7e) and (2R)-2-fluoropropanol (7b):

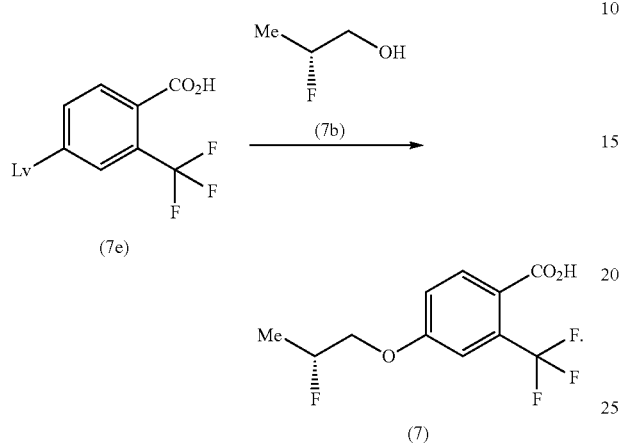

wherein Lv represents a leaving group and Me represents methyl; or (Z-3) a method for producing the compound of formula (7) shown in a reaction scheme below, consisting of:
a step of producing a compound of formula (7g) from a compound of formula (7i) and (S)-glycidyl 3-nitrobenzenesulfonate (7h),
a step of producing a compound of formula (7f) by hydrogenation reaction of the compound of formula (7g), and
a step of producing the compound of formula (7) from the compound of formula (7f):

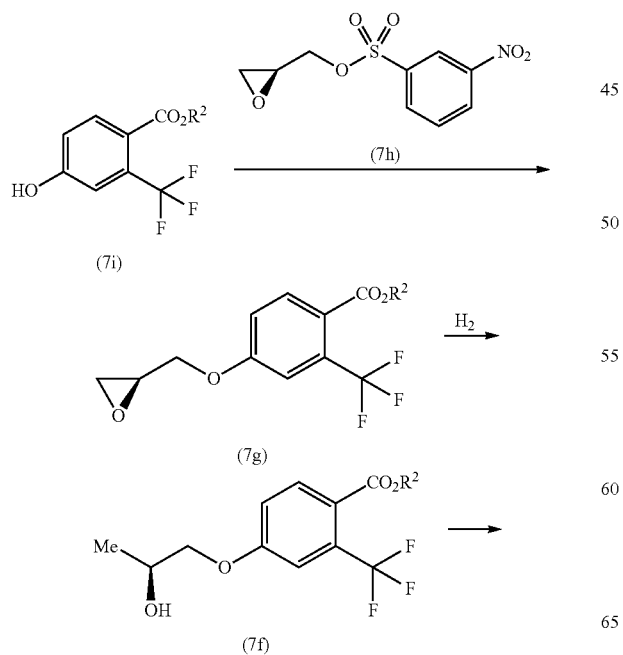

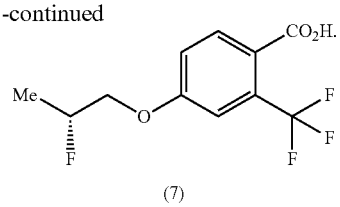

wherein $R^2$ represents lower alkyl and Me represents methyl.

7. The method for producing a compound of formula (1)

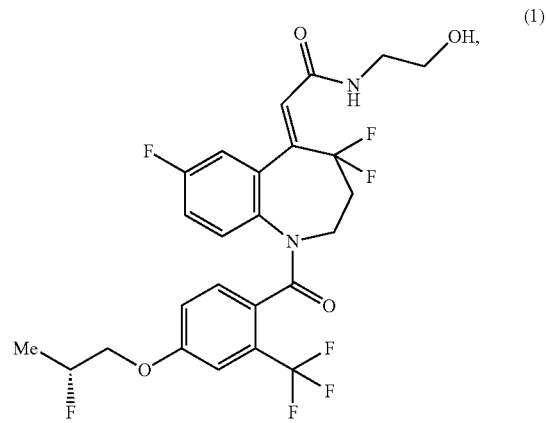 [SMILES: C[C@@H](F)COc1ccc(C(=O)N2CCC(F)(F)/C(=C\C(=O)NCCO)c3cc(F)ccc32)c(C(F)(F)F)c1]

comprising using the compound of formula (8) produced by the method shown in (X-1) according to claim 3 and a compound of formula (7) produced by a reaction scheme below, consisting of:
a step of producing a compound of formula (7a) from a compound of formula (7c) and (2R)-2-fluoropropanol (7b), and
a step of producing a compound of formula (7) from the compound of formula (7a):

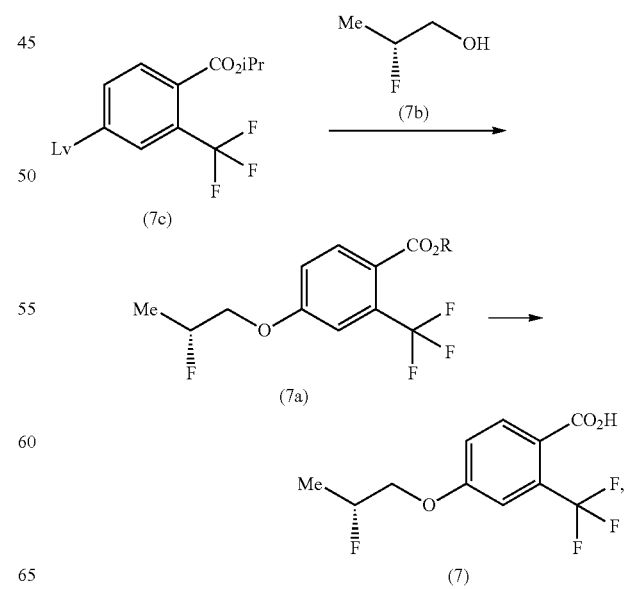

wherein Lv represents leaving group, Me represents methyl, iPr represents isopropyl, and R represents isopropyl or (2R)-2-fluoropropyl.

8. The method for producing a compound of formula (1) according to claim 2,

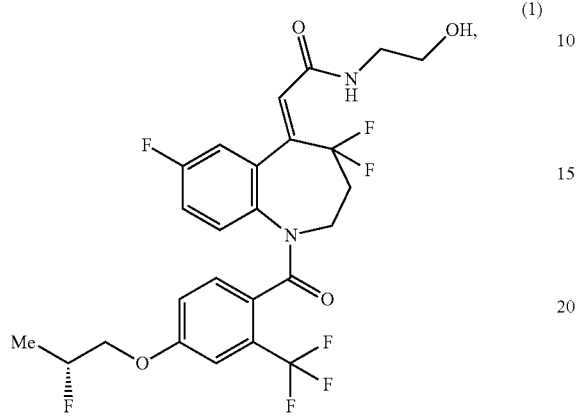

(1)

comprising using the compound of formula (8) produced by the method shown in (X-2) according to claim 3 and a compound of formula (7) produced by a reaction scheme below, consisting of:
- a step of producing a compound of formula (7a) from a compound of formula (7c) and (2R)-2-fluoropropanol (7b), and
- a step of producing a compound of formula (7) from the compound of formula (7a):

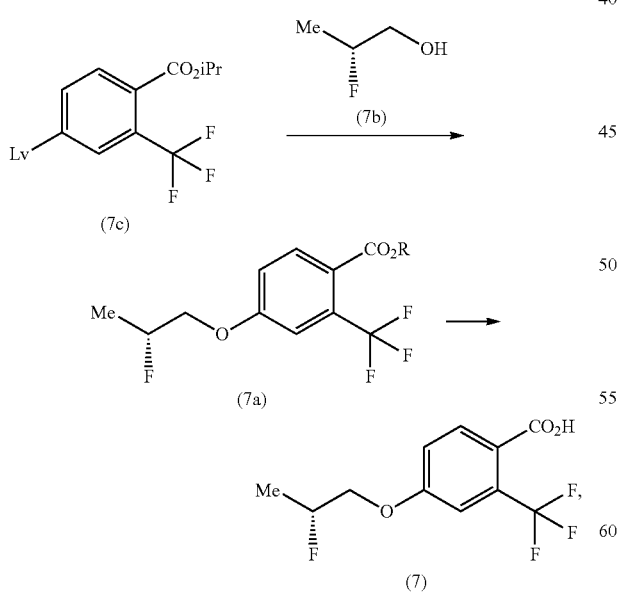

wherein Lv represents leaving group, Me represents methyl, iPr represents isopropyl, and R represents isopropyl or (2R)-2-fluoropropyl.

9. The method for producing a compound of formula (1)

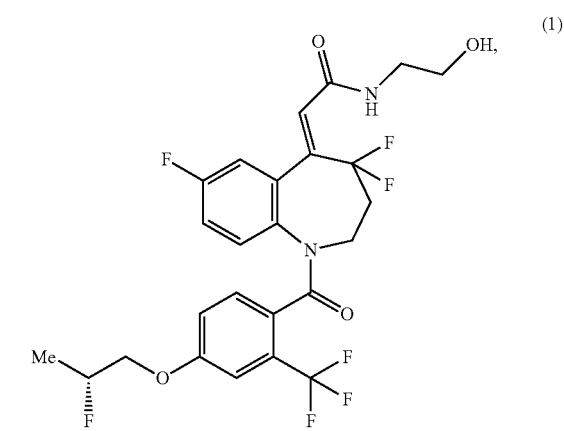 [SMILES: C[C@@H](F)COc1ccc(C(=O)N2CCC(F)(F)/C(=C\C(=O)NCCO)c3cc(F)ccc32)c(C(F)(F)F)c1]

(1)

comprising using the compound of formula (8) produced by the method shown in (X-1) according to claim 3 and compound of formula (7) produced by a reaction scheme below, which is
a step of producing the compound of formula (7) from the compound of formula (7e) and (2R)-2-fluoropropanol (7b):

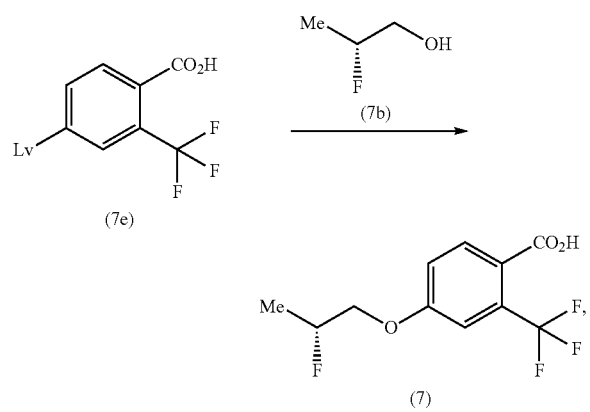

wherein Lv represents a leaving group and Me represents methyl.

10. The method for producing a compound of formula (1)

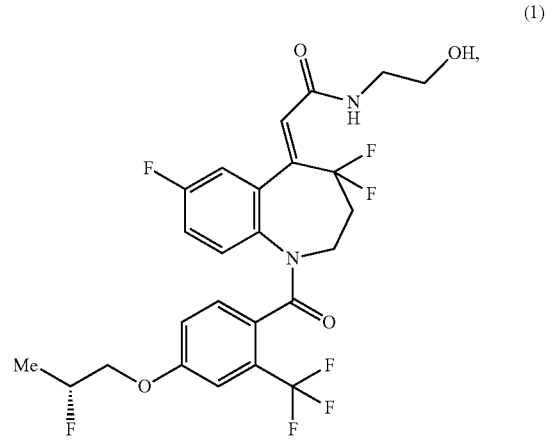 [SMILES: C[C@@H](F)COc1ccc(C(=O)N2CCC(F)(F)/C(=C\C(=O)NCCO)c3cc(F)ccc32)c(C(F)(F)F)c1]

(1)

comprising using the compound of formula (8) produced by the method shown in (X-2) according to claim 3 and the compound of formula (7) produced by a reaction scheme below, which is a step of producing the compound of formula (7) from the compound of formula (7e) and (2R)-2-fluoropropanol (7b):

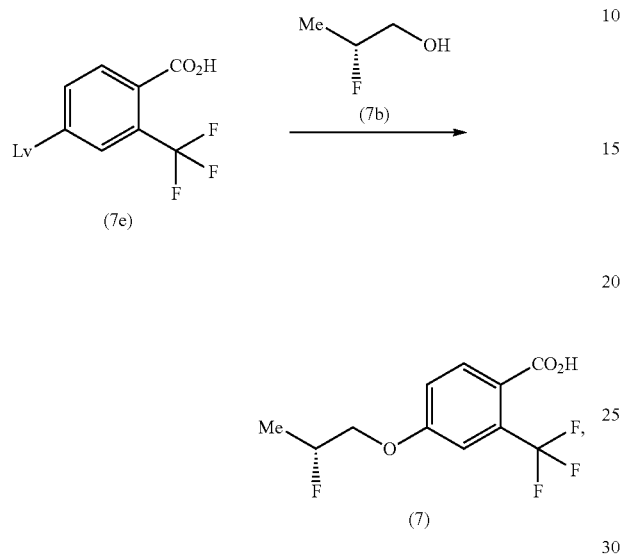

wherein Lv represents a leaving group and Me represents methyl.

11. The method for producing a compound of formula (1)

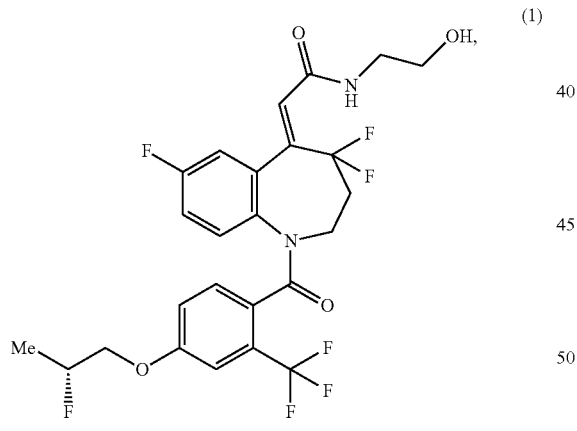

comprising using the compound of formula (8) produced by the method shown in (X-1) according to claim 3 and a compound of formula (7) produced by a reaction scheme below consisting of:

a step of producing a compound of formula (7g) from a compound of formula (7i) and (S)-glycidyl 3-nitrobenzenesulfonate (7h), a step of producing a compound of formula (7f) by hydrogenation reaction of the compound of formula (7g), and a step of producing the compound of formula (7) from the compound of formula (7f):

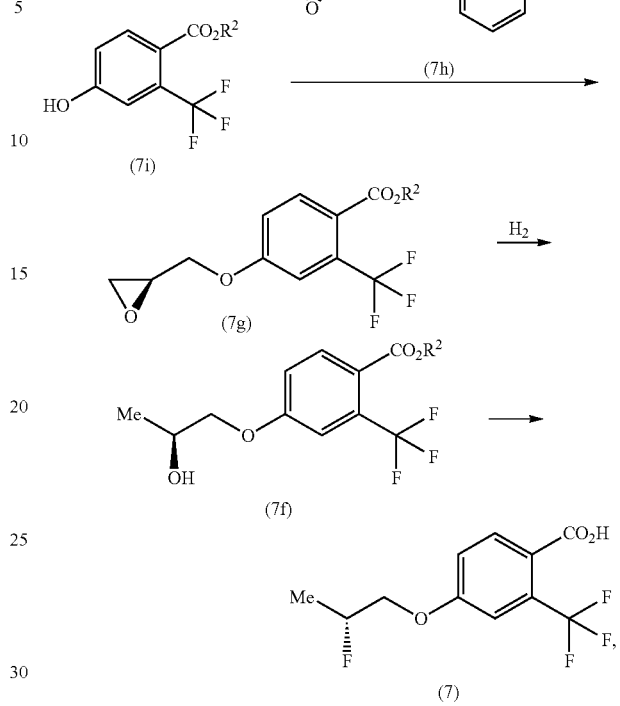

wherein $R^2$ represents lower alkyl and Me represents methyl.

12. The method for producing a compound of formula (1)

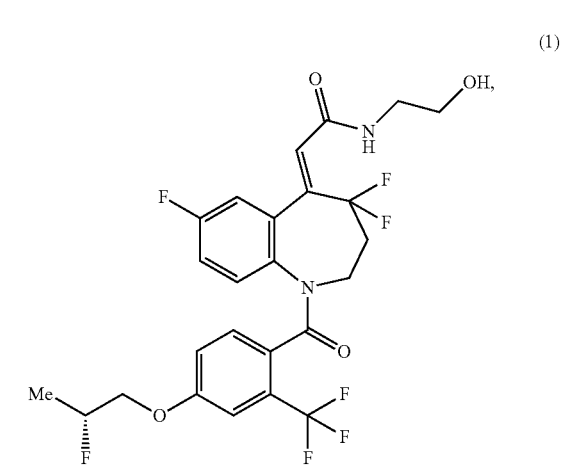 [SMILES: C[C@@H](F)COc1ccc(C(=O)N2CCC(F)(F)/C(=C\C(=O)NCCO)c3cc(F)ccc32)c(C(F)(F)F)c1]

comprising using the compound of formula (8) produced by the method shown in (X-2) according to claim 3 and a compound of formula (7) produced by a reaction scheme below consisting of:

a step of producing a compound of formula (7g) from a compound of formula (7i) and (S)-glycidyl 3-nitrobenzenesulfonate (7h), a step of producing a compound of formula (7f) by hydrogenation reaction of the compound of formula (7g), and a step of producing the compound of formula (7) from the compound of formula (7f):

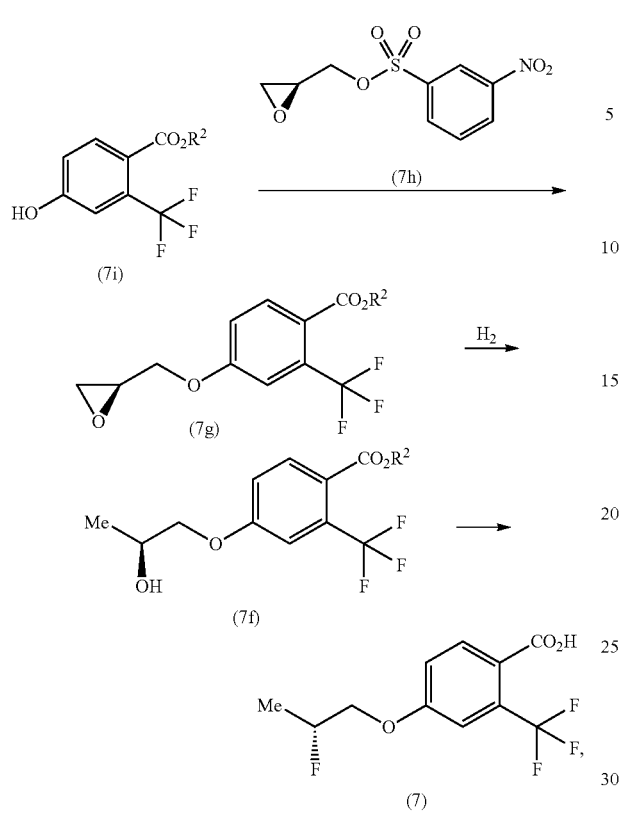

wherein R² represents lower alkyl and Me represents methyl.

13. The method for producing the compound of formula (1) according to any one of claims 7 to 12, using the compound of formula (11) produced by a method shown in a reaction scheme below, consisting of:
- a step of producing a compound of formula (14) from a compound of formula (16) and methyl 4-chlorobutyrate (15),
- a step of producing a compound of formula (13) from the compound of formula (14),
- a step of producing a compound of formula (12) from the compound of formula (13), and
- a step of producing the compound of formula (11) from the compound of formula (12):

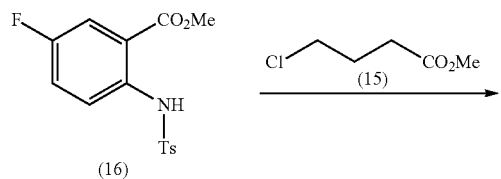

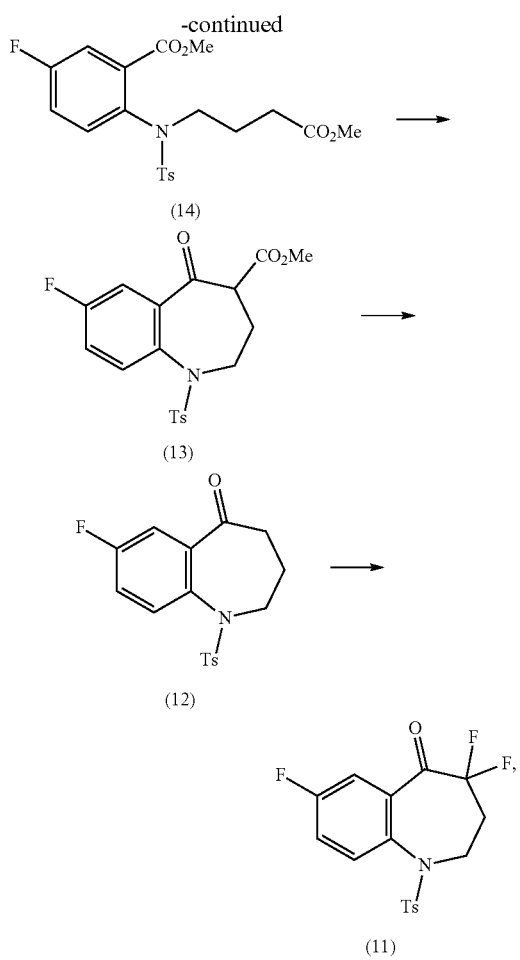

wherein Ts represents p-toluenesulfonyl and Me represents methyl.

14. The method for producing the compound of formula (1) according to claim 13, wherein in the production method (Y-1), the compound of formula (13) is produced without isolating the compound of formula (14), and the compound of formula (12) is produced without isolating the compound of formula (13).

15. (2Z)-{4,4,7-Trifluoro-1-[4-{[(2R)-2-fluoropropyl]oxy}-2-(trifluoromethyl)benzoyl]-1,2,3,4-tetrahydro-5H-1-benzazepin-5-ylidene}acetyl chloride.

16. Methyl 5-fluoro-2-{(4-methoxy-4-oxobutyl)[(4-methylphenyl)sulfonyl]amino}benzoate.

* * * * *